(12) United States Patent
Roberts et al.

(10) Patent No.: US 11,566,081 B2
(45) Date of Patent: *Jan. 31, 2023

(54) ANTI-ACETAMINOPHEN ANTIBODIES AND ACETAMINOPHEN PROTEIN ADDUCTS

(71) Applicants: BioVentures, LLC, Little Rock, AR (US); Arkansas Children's Research Institute, Little Rock, AR (US)

(72) Inventors: Dean W. Roberts, Little Rock, AR (US); Laura James, Little Rock, AR (US); Jack Hinson, Little Rock, AR (US)

(73) Assignees: BioVentures, LLC, Little Rock, AR (US); Arkansas Children's Research Institute, Little Rock, AR (US)

( * ) Notice: Subject to any disclaimer, the term of this patent is extended or adjusted under 35 U.S.C. 154(b) by 274 days.

This patent is subject to a terminal disclaimer.

(21) Appl. No.: 16/740,030

(22) Filed: Jan. 10, 2020

(65) Prior Publication Data

US 2020/0131278 A1 Apr. 30, 2020

Related U.S. Application Data

(62) Division of application No. 15/532,418, filed as application No. PCT/US2015/063786 on Dec. 3, 2015, now Pat. No. 10,570,216.

(60) Provisional application No. 62/086,923, filed on Dec. 3, 2014.

(51) Int. Cl.
| | |
|---|---|
| *C07K 16/44* | (2006.01) |
| *G01N 33/53* | (2006.01) |
| *G01N 33/94* | (2006.01) |
| *C07K 19/00* | (2006.01) |

(52) U.S. Cl.
CPC ............ *C07K 16/44* (2013.01); *G01N 33/53* (2013.01); *G01N 33/9486* (2013.01); *C07K 19/00* (2013.01)

(58) Field of Classification Search
CPC .... G01N 33/9486; G01N 33/53; C07K 16/44; C07K 19/00
See application file for complete search history.

(56) References Cited

U.S. PATENT DOCUMENTS

| | | | |
|---|---|---|---|
| 5,103,021 | A | 4/1992 | Pyare |
| 5,620,890 | A | 4/1997 | Kamps-Holtzapple et al. |
| 5,747,352 | A | 5/1998 | Yan et al. |
| 6,054,303 | A | 4/2000 | Davalian et al. |
| 6,352,862 | B1 | 3/2002 | Davis et al. |
| 7,700,740 | B2 | 4/2010 | Garvia-Martinez et al. |
| 10,351,897 | B2 | 7/2019 | James et al. |
| 10,570,216 | B2 | 2/2020 | Roberts et al. |
| 2004/0185040 | A1 | 9/2004 | Garcia-Martinez et al. |
| 2005/0136552 | A1 | 6/2005 | Buechler |
| 2009/0263839 | A1 | 10/2009 | James et al. |
| 2011/0004955 | A1 | 1/2011 | Abad et al. |
| 2011/0214205 | A1 | 9/2011 | Dietrich et al. |
| 2012/0171699 | A1 | 7/2012 | Goodman et al. |
| 2012/0246748 | A1 | 9/2012 | Guo et al. |
| 2012/0301897 | A1 | 11/2012 | James et al. |
| 2012/0322073 | A1 | 12/2012 | Lopez-Girona et al. |
| 2013/0029322 | A1 | 1/2013 | Jansen-Durr et al. |
| 2013/0287783 | A1 | 10/2013 | Frank et al. |
| 2013/0333061 | A1 | 12/2013 | Wu et al. |
| 2017/0175166 | A1 | 6/2017 | James et al. |
| 2017/0362340 | A1 | 12/2017 | Roberts et al. |
| 2019/0300931 | A1 | 10/2019 | James et al. |

FOREIGN PATENT DOCUMENTS

| | | |
|---|---|---|
| EP | 0095229 A2 | 11/1983 |
| WO | 1988008534 A1 | 11/1988 |
| WO | 2009131998 A1 | 10/2009 |
| WO | 2015123574 A1 | 8/2015 |
| WO | 2016090163 A2 | 6/2016 |
| WO | 2016090163 A3 | 6/2016 |

OTHER PUBLICATIONS

Bartolone, J. et al., "Immunochemical Detection of Acetaminophen-Bound Liver Proteins," Biochem. Pharmacol., 1987, pp. 1193-1196, vol. 36, No. 8.

Bartolone, J. et al., "Immunochemical Analysis of Acetaminophen Covalent Binding to Proteins, Partial Characterization of the Major Acetaminophen-Binding Liver Proteins. Partial Characterization of the Major Acetaminophen-Binding Liver Proteins," Biochem. Pharmacol., 1988, pp. 4763-4774, vol. 37, No. 24, Pergamon Press plc, Great Britain.

Betowski, L. et al., "Direct Analysis of Rat Bile for Acetaminophen and Two of its Conjugated Metabolites via Thermospray Liquid Chromatography/Mass Spectrometry," Biomedical and Environmental Mass Spectrometry, 1987, pp. 705-709, vol. 14, No. 12.

Chaudhuri, S. et al., "Acetaminophen hepatotoxicity and HIF-1α induction in mice occurs without hypoxia," Toxicol. Appl. Pharmacol., May 1, 2011, pp. 211-220, vol. 252, No. 3.

Chothia, C. et al., "Canonical Structures for the Hypervariable Regions of Immunoglobulins," J. Mol. Biol., 1987, pp. 901-917, vol. 196, Academic Press Limited.

Chothia, C. et al., "Conformations of immunoglobulin hypervariable regions," Nature, Dec. 1989, pp. 878-883, vol. 342, Nature Publishing Group.

Coles, B. et al., "The Spontaneous and Enzymatic Reaction of N-Acetyl-p-benzoquinonimine with Glutathione: A Stopped-Flow Kinetic Study," Archives of Biochemistry and Biophysics, Jul. 1988, pp. 253-260, vol. 264, No. 1.

Communication under Rule 71(3) EPC (Notice of Allowance) dated Mar. 25, 2019 from related European Patent Application No. 15748750.5; 7 pgs.

Davern, T. et al., "Measurement of Serum Acetaminophen-Protein Adducts in Patients With Acute Liver Failure," Gastroenterology, 2006, pp. 687-694, vol. 130, No. 3.

(Continued)

*Primary Examiner* — Shafiqul Haq
(74) *Attorney, Agent, or Firm* — Polsinelli PC

(57) ABSTRACT

The present disclosure provides isolated antibodies that bind to acetaminophen-protein adducts that are useful in the detection and diagnosis of acetaminophen-induced toxicity.

9 Claims, 6 Drawing Sheets
(6 of 6 Drawing Sheet(s) Filed in Color)
Specification includes a Sequence Listing.

(56) References Cited

OTHER PUBLICATIONS

Extended European Search Report dated May 6, 2011 from related European Patent Application No. 09735343.7; 9 pgs.
Extended European Search Report dated Oct. 25, 2017 from related European Patent Application No. 15748750.5; 8 pgs.
Extended European Search Report dated May 16, 2018 from related European Patent Application No. 15865732.0; 9 pgs.
Ferguson, D. et al., "Acetaminophen-Induced Alterations in Pancreatic β Cells and Serum Insulin Concentrations in B6C3F1 Mice," Toxicology and Applied Pharmacology, 1990, pp. 225-243, vol. 104, No. 2.
Fountoulakis, M. et al., "Two-dimensional database of mouse liver proteins: Changes in hepatic protein levels following treatment with acetaminophen or its nontoxic regioisomer 3-acetamidophenol," Electrophoresis, 2000, pp. 2148-2161, vol. 21, Wiley-VCH Verlag GmbH, Weinheim.
Getek, T. et al., "Utility of Solution Electrochemistry Mass Spectrometry for Investigating the Formation and Detection of Biologically Important Conjugates of Acetaminophen," Journal of Chromatography, 1989, pp. 245-256, vol. 474, No. 1.
Gibson, J. et al., "Mechanism of Acetaminophen-Induced Hepatotoxicity: Covalent Binding versus Oxidative Stress," Chem. Res. Toxicol., 1996, pp. 58-585, vol. 9, No. 3.
Gillette, J. et al., "Formation of Chemically Reactive Metabolites of Phenacetin and Acetaminophen," Biological Reactive Intermediates-II, Chemical Mechanisms and Biological Effects Part B, Adv. Exp. Med. Biol., 1981, pp. 931-950, vol. 136.
Halmes, N. et al., "Glutamate Dehydrogenase Covalently Binds to a Reactive Metabolite of Acetaminophen," Chem. Res. Toxicol., 1996, pp. 541-546, vol. 9, No. 2.
Halmes, N. et al., "The acetaminophen regioisomer 3'-hydroxyacetanilide inhibits and covalently binds to cytochrome P450 2E1," Toxicology Letters, 1998, pp. 65-71, vol. 94, No. 1.
Heard, K. et al., "Acetaminophen-cysteine adducts during therapeutic dosing and following overdose," BMC Gastroenterology, 2011, pp. 1-9, vol. 11, No. 20.
Hinson, J. et al., "Studies on the Microsomal Formation of Arylating Metabolites of Acetaminophen and Phenacetin," Molecular Pharmacology, 1977, pp. 625-633, vol. 13.
Hinson, J. et al., "Kinetic Evidence of Multiple Chemically Reactive Intermediates in the Breakdown of Phenacetin N—O-Glucuronide," Pharmacology, 1979, pp. 237-248, vol. 19.
Hinson, J. et al., "Metabolism of [p-18O]-Phenacetin: The Mechanism of Activation of Phenacetin to Reactive Metabolites in Hamsters," Molecular Pharmacology, 1979, pp. 419-427, vol. 15.
Hinson, J. et al., "N-Hydroxyacetaminophen: A Microsomal Metabolite of N-Hydroxyphenacetin But Apparently Not of Acetaminophen," Life Sciences, 1979, pp. 2133-2138, vol. 24.
Hinson, J. et al., "3-Hydroxyacetaminophen: A Microsomal Metabolite of Acetaminophen: Evidence Against an Epoxide as the Reactive Metabolite of Acetaminophen," Drug Metabolism and Disposition, 1980, pp. 289-294, vol. 8, No. 5.
Hinson, J. et al., "A Simple High-Pressure Liquid Chromatographic Assay for the N-Hydroxy Derivatives of Phenacetin, Acetaminophen, 2-Acetylaminofluorene, and Other Hydroxamic Acids," Analytical Biochemistry, 1980, pp. 462-467, vol. 101.
Hinson, J. et al., "Acetaminophen-induced hepatotoxicity," Life Sciences, Jul. 13, 1981, pp. 107-116, vol. 29, No. 2 (abstract only).
Hinson, J. et al., "3-(Glutathion-S-yl)acetaminophen: A Biliary Metabolite of Acetaminophen," Drug Metabolism and Disposition, 1982, pp. 47-50, vol. 10, No. 1.
Hinson, J. et al., "Acetaminophen-Induced Hepatic Glycogen Depletion and Hyperglycemia in Mice," Biochemical Pharmacology, 1983, pp. 1979-1988, vol. 32, No. 13, Pergamon Press Ltd, Great Britain.
Hinson, J., "Reactive Metabolites of Phenacetin and Acetaminophen: A Review," Environmental Health Perspectives, 1983, pp. 71-79, vol. 49.

Hinson, J. et al., "Acetaminophen-Induced Alterations in Blood Glucose and Blood Insulin Levels in Mice," Research Communications in Chemical Pathology and Pharmacology, Mar. 1984, vol. 43, No. 3.
Hinson, J. et al., "Mechanism of paracetamol toxicity," The Lancet, Mar. 24, 1990, p. 732, vol. 335, No. 8691.
Hinson, J. et al., "Phase II enzymes and bioactivation," Can. J. Physiol. Pharmacol., 1995, pp. 1407-1413, vol. 73, No. 10, Printed in Canada.
Hinson, J. et al., "Mechanisms of Acetaminophen Toxicity: Immunochemical Detection of Drug-Protein Adducts," Drug Metabolism Reviews, 1995, pp. 73-92, vol. 27, Nos. 1 & 2.
Hinson, J. et al., "Immunochemical Detection of Drug-Protein Adducts in Acetaminophen Hepatotoxicity," Adv. Exp. Med. Biol., 1996, pp. 47-55, vol. 387.
Hinson, J. et al., "Nitrotyrosine-Protein Adducts in Hepatic Centrilobular Areas following Toxic Doses of Acetaminophen in Mice," Chem. Res. Toxicol., 1998, pp. 604-607, vol. 11, No. 6.
Hinson, J. et al., "Western Blot Analysis for Nitrotyrosine Protein Adducts in Livers of Saline-Treated and Acetaminophen-Treated Mice," Toxicological Sciences, 2000, pp. 467-473, vol. 53, No. 2.
Hinson, J. et al., "Mechanisms of Acetaminophen-Induced Liver Necrosis," Handb. Exp. Pharmacol., 2010, pp. 369-405, vol. 196 (author manuscript only).
Hu, Z. et al., "Quantitative Liver-Specific Protein Fingerprint in Blood: A Signature for Hepatotoxicity," Theranostics, 2014, pp. 215-228, vol. 4, No. 2, Ivyspring International Publisher.
International Search Report and Written Opinion dated Jun. 19, 2009 from related PCT Patent Application No. PCT/US2009/041247; 10 pgs.
International Search Report and Written Opinion dated May 18, 2015 from related PCT Patent Application No. PCT/US2015/015905; 8 pgs.
International Search Report and Written Opinion dated Feb. 25, 2016 from related PCT Patent Application No. PCT/US2015/063786; 15 pgs.
James, L. et al., "Evaluation of Occult Acetaminophen Hepatotoxicity in Hospitalized Children Receiving Acetaminophen," Clin. Pediatr., 2001, pp. 243-248, vol. 40.
James, L. et al., "Effect of N-Acetylcysteine on Acetaminophen Toxicity in Mice: Relationship to Reactive Nitrogen and Cytokine Formation," Toxicological Sciences, 2003, pp. 458-467, vol. 75.
James, L. et al., "Correlation of MCP1 with Toxicity of Acetaminophen Overdose," Journal of the University of Arkansas for Medical Sciences, Jun. 2004, pp. 424-425, vol. 100, No. 12.
James, L. et al., "Acetaminophen-Associated Hepatic Injury: Evaluation of Acetaminophen Protein Adducts in Children and Adolescents With Acetaminophen Overdose," NIH Public Access Author Manuscript, 17 pgs., Clin. Pharmacol. Ther., Dec. 2008, pp. 684-690, vol. 84, No. 6.
James, L. et al., "Pharmacokinetics of Acetaminophen-Protein Adducts in Adults with Acetaminophen Overdose and Acute Liver Failure," Drug Metabolism and Disposition, 2009, pp. 1779-1784, vol. 37, No. 8.
James, L. et al., "Acetaminophen-Induced Hepatotoxicity," Drug. Metab. Dis., 2003, pp. 1499-1506, vol. 31, No. 12, The American Society for Pharmacology and Experimental Therapeutics, USA.
Keller, R. et al., "Mechanism of Acetaminophen-Stimulated NADPH Oxidation Catalyzed by the Peroxidase-H2O2 System," Drug Metabolism and Disposition, 1991, pp. 184-187, vol. 19, No. 1.
Matthews, A. et al., "Acetaminophen-Induced Hepatotoxicity, Analysis of Total Covalent Binding Vs. Specific Binding to Cysteine," Drug Metabolism and Disposition, 1996, pp. 1992-1196, vol. 24, No. 11.
Matthews, A. et al., "Comparison of covalent binding of acetaminophen and the regioisomer 3'-hydroxyacetanilide to mouse liver protein," Toxicology Letters, 1997, pp. 77-82, vol. 90.
Merrick, B. et al., "Alterations in the Rat Serum Proteome during Liver Injury from Acetaminophen Exposure," JPET, 2006, pp. 792-802, vol. 318, No. 2, USA.

(56) References Cited

OTHER PUBLICATIONS

Michael, S. et al., "Pretreatment of Mice with Macrophage Inactivators Decreases Acetaminophen Hepatotoxicity and the Formation of Reactive Oxygen and Nitrogen Species," Hepatology, 1999, pp. 186-195, vol. 30, No. 1.
Mulder, G. et al., "Conversion of the N—O-Glucuronide and N—O-Sulfate Conjugates of N-Hydroxy-Phenacetin to Reactive Intermediates," Biochemical Pharmacology, 1978, pp. 1641-1649, vol. 27, Pergamon Press Ltd., Great Britain.
Muldrew, K. et al., "Determination Of Acetaminophen-Protein Adducts in Mouse Liver and Serum and Human Serum After Hepatotoxic Doses of Acetaminophen Using High-Performance Liquid Chromatography With Electrochemical Detection," Drug Metabolism and Disposition, 2002, pp. 446-451, vol. 30, No. 4.
Notice of Acceptance dated Sep. 2, 2019 from related Australian Patent Application No. 2015218355; 6 pgs.
Notice of Allowance dated Mar. 7, 2019 from related U.S. Appl. No. 15/118,297; 11 pgs.
Notice of Allowance dated Oct. 10, 2019 from related U.S. Appl. No. 15/532,418; 8 pgs.
Office Action dated Feb. 21, 2012 from related U.S. Appl. No. 12/427,434; 8 pgs.
Office Action dated May 10, 2012 from related U.S. Appl. No. 12/427,434; 8 pgs.
Office Action dated Sep. 30, 2011 from related U.S. Appl. No. 12/427,434; 8 pgs.
Office Action dated Sep. 10, 2012 from related European Patent Application No. 09735343.7; 6 pgs.
Office Action dated Jul. 20, 2018 from related U.S. Appl. No. 15/118,297; 9 pgs.
Office Action dated Aug. 24, 2018 from related European Patent Application No. 15748750.5; 4 pgs.
Office Action dated Oct. 23, 2018 from related Japanese Patent Application No. 2016-569567; 4 pgs.
Office Action dated Nov. 20, 2018 from related U.S. Appl. No. 15/118,297; 9 pgs.
Office Action dated Apr. 8, 2019 from related European Patent Application No. 15865732.0; 5 pgs.
Office Action dated May 9, 2019 from related U.S. Appl. No. 15/532,418; 15 pgs.
Office Action dated Apr. 26, 2019 from related Australian Patent Application No. 2015218355; 3 pgs.
Office Action dated Jul. 23, 2019 from related Japanese Patent Application No. 2017-548368; 9 pgs.
Pang, K. et al., "High-Performance Liquid Chromatographic Assay for Acetaminophen and Phenacetin in the Presence of Their Metabolites in Biological Fluids," J. Chromatography, 1979, pp. 165-175, vol. 174.
Partial Supplementary European Search Report dated Jul. 19, 2017 from related European Patent Application No. 15748750.5; 11 pgs.
Peters, T., "Serum Albumin: Recent Progress in the Understanding of Its Structure and Biosynthesis," Clin. Chem., 1977, pp. 5-12, vol. 23, No. 1.
Potter, D. et al., "Identification of Acetaminophen Polymerization Products Catalyzed by Horseradish Peroxidase," J. Biol. Chem., Oct. 5, 1985, pp. 12174-12180, vol. 260, No. 22.
Potter, D. et al., "Horseradish Peroxidase-Catalyzed Oxidation of Acetaminophen to Intermediates that Form Polymers or Conjugate with Glutathione," Molecular Pharmacology, 1986, pp. 155-162, vol. 29, No. 2.
Potter, D. et al., "Reactions of Glutathione with Oxidative Intermediates of Acetaminophen," Adv. Exp. Med. Biol., 1986, pp. 763-772, vol. 197.
Potter, D. et al., "Reactions of N-Acetyl-p-benzoquinone Imine with Reduced Glutathione, Acetaminophen, and NADPH," Molecular Pharmacology, 1986, pp. 33-41, vol. 30.
Potter, D. et al., "Mechanisms of Acetaminophen Oxidation to N-Acetyl-P-benzoquinone Imine by Horseradish Peroxidase and Cytochrome P-450," J. Biol. Chem., Jan. 25, 1987, pp. 966-973, vol. 262, No. 3.
Potter, D. et al., "The 1- and 2-Electron Oxidation of Acetaminophen Catalyzed by Prostaglandin H Synthase," J. Biol. Chem., Jan. 25, 1987, pp. 974-980, vol. 262, No. 3.
Potter, D. et al., "Epitope Characterization of Acetaminophen Bound to Protein and Nonprotein Sulfhydryl Groups by an Enzyme-Linked Immunosorbent Assay," JPET, 1989, pp. 182-189, vol. 248, No. 1.
Potter, D. et al., "Acetaminophen Peroxidation Reactions," Drug Metabolism Reviews, 1989, pp. 341-358, vol. 20, Nos. 2-4.
Pumford, N. et al., "Immunochemical Quantitation of 3-(Cystein-S-yl)acetaminophen Adducts in Serum and Liver Proteins of Acetaminophen-Treated Mice," JPET, 1989, pp. 190-196, vol. 248, No. 1.
Pumford, N. et al., "Immunochemical Quantitation of 3-(Cystein-S-yl)acetaminophen Protein Adducts in Subcellular Liver Fractions Following a Hepatotoxic Dose of Acetaminophen," Biochemical Pharmacology, 1990, pp. 573-579, vol. 40, No. 3, Pergamon Press plc, Great Britain.
Pumford, N. et al., "Immunoblot Analysis of Protein Containing 3-(Cystein-S-yl)acetaminophen Adducts in Serum and Subcellular Liver Fractions from Acetaminophen-Treated Mice," Toxicology and Applied Pharmacology, 1990, pp. 001-0012, vol. 104, No. 3, Academic Press, Inc.
Pumford, N. et al., "A Metabolite of Acetaminophen Covalently Binds to the 56 kDa Selenium Binding Protein," Biochemical and Biophysical Research Communications, Feb. 14, 1992, pp. 1348-1355, vol. 182, No. 3.
Pumford, N. et al., "Covalent Binding of Acetaminophen to N-10-Formyl-Tetrahydrofolate Dehydrogenase in Mice," JPET, 1997, pp. 501-505, vol. 280, No. 1.
Qiu, Y. et al., "Identification of the Hepatic Protein Targets of Reactive Metabolites of Acetaminophen in Vivo in Mice Using Two-dimensional Gel Electrophoresis and Mass Spectrometry," J. Biol. Chem., Jul. 10, 1998, pp. 17940-17953, vol. 273, No. 28.
Roberts, D. et al., "A Sensitive Immunochemical Assay for Acetaminophen-Protein Adducts," JPET, 1987, pp. 527-533, vol. 241, No. 2.
Roberts, D. et al., "Critical Considerations in the Immunochemical Detection and Quantitation of Antigenic Biomarkers," Biomedical and Environmental Sciences, 1991, pp. 113-129, vol. 4, Nos. 1-2.
Roberts, D. et al., "Immunohistochemical Localization and Quantification of the 3-(Cystein-S-yl)-acetaminophen Protein Adduct in Acetaminophen Hepatotoxicity," American Journal of Pathology, Feb. 1991, pp. 359-371, vol. 138, No. 2.
Rudikoff, S. et al., "Single amino acid substitution altering antigen-binding specificity," PNAS, Mar. 1982, pp. 1979-1983, vol. 79.
Salminen, W. et al., "Immunochemical Comparison of 3'-Hydroxyacetanilide and Acetaminophen Binding in Mouse Liver," Drug Metabolism and Disposition, 1998, pp. 267-271, vol. 26, No. 3.
Schnellmann, J. et al., "Deferoxamine delays the development of the hepatotoxicity of acetaminophen in mice," Toxicology Letters, 1999, pp. 79-88, vol. 106.
Song, W. et al., "One-Step Immunoassay for Acetaminophen and Salicylate in Serum, Plasma, and Whole Blood," J. Analytical Toxicology, Sep. 2003, pp. 366-371, vol. 27.
Webster, P. et al., "Acetaminophen Toxicity in Children: Diagnostic Confirmation Using a Specific Antigenic Biomarker," J Clin. Pharmacol., 1996, pp. 397-402, vol. 36.
Weeks, B. et al., "Acetaminophen Toxicity to Cultured Rat Embryos," Teratogenesis, Carcinogenesis, and Mutagenesis, 1990, pp. 361-371, vol. 10, No. 5.
Office Action dated Jul. 22, 2020 from related Australian Patent Application No. 2015358373; 5 pgs.
Communication under Rule 71(3) EPC (Notice of Allowance) dated May 15, 2020 from related European Patent Application No. 15865732; 7 pgs.
Office Action dated Mar. 12, 2020 from related European Patent Application No. 15865732.0; 5 pgs.
Office Action dated Mar. 24, 2020 from related Japanese Patent Application No. 2017-548368; 7 pgs., with English translation.
Notice of Acceptance dated May 14, 2021 from related Australian Patent Application No. 2015358373; 3 pgs.

(56) References Cited

OTHER PUBLICATIONS

Office Action dated Nov. 3, 2020 from related Canadian Patent Application No. 2,936,907; 3 pgs.
Office Action dated May 14, 2021 from related U.S. Appl. No. 16/433,657; 11 pgs.
Office Action dated Dec. 11, 2020 from related Australian Patent Application No. 2015358373; 4 pgs.
Notice of Allowance dated Dec. 17, 2021 from related Canadian Patent Application No. 2,936,907; 1 pg.
Office Action dated Oct. 22, 2021 from related Canadian Patent Application No. 2,967,037; 4 pgs.
Office Action dated Nov. 16, 2021 from related U.S. Appl. No. 16/433,657; 13 pgs.

SEQUENCE LISTING

```
<160> NUMBER OF SEQ ID NOS: 24

<210> SEQ ID NO 1
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 1

Gln Ala Ser Gln Ser Ile Ser Arg Gln Val Ser
1               5                   10

<210> SEQ ID NO 2
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 2

Arg Ala Ser Thr Leu Ala Ser
1               5

<210> SEQ ID NO 3
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 3

Leu Gly Ile Val Thr Asp Arg Ile Ala Asp Gly Leu Ala
1               5                   10

<210> SEQ ID NO 4
<211> LENGTH: 5
<212> TYPE: PRT
<213> ORGANISM: Artificial Sequence
<220> FEATURE:
<223> OTHER INFORMATION: SYNTHESIZED

<400> SEQUENCE: 4

Ala Tyr Gly Ile Asn
1               5

<210> SEQ ID NO 5
<211> LENGTH: 15
<212> TYPE: PRT
<213> ORGANISM: Artificial Sequence
<220> FEATURE:
<223> OTHER INFORMATION: SYNTHESIZED

<400> SEQUENCE: 5

Phe Ser Ala Pro His Thr Ala Ser Tyr Ala Arg Trp Thr Lys Gly
1               5                   10                  15

<210> SEQ ID NO 6
```

```
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 6

Tyr Asp Arg Gly Gly Met Val Phe Asn Leu
1               5                   10

<210> SEQ ID NO 7
<211> LENGTH: 13
<212> TYPE: PRT
<213> ORGANISM: Artificial Sequence
<220> FEATURE:
<223> OTHER INFORMATION: SYNTHESIZED

<400> SEQUENCE: 7

Gln Ser Ser Gln Asn Val Phe Arg Lys Asn Tyr Leu Ser
1               5                   10

<210> SEQ ID NO 8
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 8

Tyr Ile Asp Ser Leu Thr Ser
1               5

<210> SEQ ID NO 9
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 9

Leu Gly Val Asp Gly Ser Ala Asn Asp Ala Thr
1               5                   10

<210> SEQ ID NO 10
<211> LENGTH: 5
<212> TYPE: PRT
<213> ORGANISM: Artificial Sequence
<220> FEATURE:
<223> OTHER INFORMATION: SYNTHESIZED

<400> SEQUENCE: 10

Asn Tyr Tyr Ile Ile
1               5

<210> SEQ ID NO 11
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 11

Ile Thr Tyr Gly Gly Gly Phe Ala Tyr Tyr Ala Ser Trp Ala Lys Gly
1               5                   10                  15

<210> SEQ ID NO 12
<211> LENGTH: 9
```

```
<212> TYPE: PRT
<213> ORGANISM: Artificial Sequence
<220> FEATURE:
<223> OTHER INFORMATION: SYNTHESIZED

<400> SEQUENCE: 12

Ala Ala Ala Gly Gly Ala Tyr Asp Leu
1               5

<210> SEQ ID NO 13
<211> LENGTH: 237
<212> TYPE: PRT
<213> ORGANISM: Artificial Sequence
<220> FEATURE:
<223> OTHER INFORMATION: SYNTHESIZED

<400> SEQUENCE: 13

Met Asp Thr Arg Ala Pro Thr Gln Leu Leu Gly Leu Leu Leu Leu Trp
1               5                   10                  15

Leu Pro Gly Ala Thr Phe Ala Leu Val Met Thr Gln Thr Pro Ser Ser
                20                  25                  30

Val Pro Ala Ala Val Gly Gly Thr Val Thr Ile Gly Cys Gln Ala Ser
            35                  40                  45

Gln Ser Ile Ser Arg Gln Val Ser Trp Tyr Gln Gln Lys Pro Gly Gln
    50                  55                  60

Pro Pro Lys Leu Leu Ile Tyr Arg Ala Ser Thr Leu Ala Ser Gly Val
65                  70                  75                  80

Ser Ser Arg Phe Lys Gly Ser Gly Ser Gly Thr Glu Phe Thr Leu Thr
                85                  90                  95

Ile Ser Gly Val Gln Cys Asp Asp Ala Ala Thr Tyr Tyr Cys Leu Gly
            100                 105                 110

Ile Val Thr Asp Arg Ile Ala Asp Gly Leu Ala Phe Gly Gly Gly Thr
        115                 120                 125

Glu Val Val Val Lys Gly Asp Pro Val Ala Pro Thr Val Leu Ile Phe
    130                 135                 140

Pro Pro Ala Ala Asp Gln Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235

<210> SEQ ID NO 14
<211> LENGTH: 456
<212> TYPE: PRT
<213> ORGANISM: Artificial Sequence
<220> FEATURE:
<223> OTHER INFORMATION: SYNTHESIZED

<400> SEQUENCE: 14

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
```

```
                20                  25                  30
Gly Thr Pro Leu Thr Leu Thr Cys Thr Val Ser Gly Phe Ser Ile Asn
            35                  40                  45
Ala Tyr Gly Ile Asn Trp Val Arg Gln Ala Pro Gly Lys Gly Leu Glu
    50                  55                  60
Tyr Ile Gly Phe Ser Ala Pro His Thr Ala Ser Tyr Ala Arg Trp Thr
65                  70                  75                  80
Lys Gly Arg Phe Thr Met Ser Arg Thr Ser Thr Val Asp Leu Arg
                85                  90                  95
Met Thr Ser Pro Thr Thr Glu Asp Thr Ala Thr Tyr Phe Cys Ala Arg
            100                 105                 110
Tyr Asp Arg Gly Gly Met Val Phe Asn Leu Trp Gly Gln Gly Thr Leu
            115                 120                 125
Val Thr Val Ser Ser Gly Gln Pro Lys Ala Pro Ser Val Phe Pro Leu
            130                 135                 140
Ala Pro Cys Cys Gly Asp Thr Pro Ser Ser Thr Val Thr Leu Gly Cys
145                 150                 155                 160
Leu Val Lys Gly Tyr Leu Pro Glu Pro Val Thr Val Thr Trp Asn Ser
                165                 170                 175
Gly Thr Leu Thr Asn Gly Val Arg Thr Phe Pro Ser Val Arg Gln Ser
            180                 185                 190
Ser Gly Leu Tyr Ser Leu Ser Ser Val Val Ser Val Thr Ser Ser Ser
            195                 200                 205
Gln Pro Val Thr Cys Asn Val Ala His Pro Ala Thr Asn Thr Lys Val
    210                 215                 220
Asp Lys Thr Val Ala Pro Ser Thr Cys Ser Lys Pro Thr Cys Pro Pro
225                 230                 235                 240
Pro Glu Leu Leu Gly Gly Pro Ser Val Phe Ile Phe Pro Pro Lys Pro
                245                 250                 255
Lys Asp Thr Leu Met Ile Ser Arg Thr Pro Glu Val Thr Cys Val Val
            260                 265                 270
Val Asp Val Ser Gln Asp Asp Pro Glu Val Gln Phe Thr Trp Tyr Ile
            275                 280                 285
Asn Asn Glu Gln Val Arg Thr Ala Arg Pro Pro Leu Arg Glu Gln Gln
            290                 295                 300
Phe Asn Ser Thr Ile Arg Val Val Ser Thr Leu Pro Ile Ala His Gln
305                 310                 315                 320
Asp Trp Leu Arg Gly Lys Glu Phe Lys Cys Lys Val His Asn Lys Ala
                325                 330                 335
Leu Pro Ala Pro Ile Glu Lys Thr Ile Ser Lys Ala Arg Gly Gln Pro
            340                 345                 350
Leu Glu Pro Lys Val Tyr Thr Met Gly Pro Pro Arg Glu Glu Leu Ser
            355                 360                 365
Ser Arg Ser Val Ser Leu Thr Cys Met Ile Asn Gly Phe Tyr Pro Ser
    370                 375                 380
Asp Ile Ser Val Glu Trp Glu Lys Asn Gly Lys Ala Glu Asp Asn Tyr
385                 390                 395                 400
Lys Thr Thr Pro Ala Val Leu Asp Ser Asp Gly Ser Tyr Phe Leu Tyr
                405                 410                 415
Ser Lys Leu Ser Val Pro Thr Ser Glu Trp Gln Arg Gly Asp Val Phe
            420                 425                 430
Thr Cys Ser Val Met His Glu Ala Leu His Asn His Tyr Thr Gln Lys
            435                 440                 445
```

```
Ser Ile Ser Arg Ser Pro Gly Lys
    450                 455

<210> SEQ ID NO 15
<211> LENGTH: 237
<212> TYPE: PRT
<213> ORGANISM: Artificial Sequence
<220> FEATURE:
<223> OTHER INFORMATION: SYNTHESIZED

<400> SEQUENCE: 15

Met Asp Thr Arg Ala Pro Thr Gln Leu Leu Gly Leu Leu Leu Leu Trp
1               5                   10                  15

Leu Pro Gly Ala Thr Phe Ala Ile Glu Met Thr Gln Thr Pro Ser Pro
            20                  25                  30

Val Ser Ala Val Val Gly Gly Thr Val Thr Ile Asn Cys Gln Ser Ser
        35                  40                  45

Gln Asn Val Phe Arg Lys Asn Tyr Leu Ser Trp Phe Gln Gln Lys Pro
    50                  55                  60

Gly Gln Pro Pro Lys Leu Leu Ile Ser Tyr Ile Asp Ser Leu Thr Ser
65                  70                  75                  80

Gly Val Pro Ser Arg Phe Ser Gly Ser Gly Ala Gly Thr Gln Phe Thr
                85                  90                  95

Leu Thr Ile Ser Asp Val Gln Cys Asp Asp Ala Ala Thr Tyr Tyr Cys
            100                 105                 110

Leu Gly Val Asp Gly Ser Ala Asn Asp Ala Thr Phe Gly Gly Gly Thr
        115                 120                 125

Glu Val Val Val Glu Gly Asp Pro Val Ala Pro Thr Val Leu Ile Phe
    130                 135                 140

Pro Pro Ala Ala Asp Gln Val Ala Thr Gly Thr Val Thr Ile Val Cys
145                 150                 155                 160

Val Ala Asn Lys Tyr Phe Pro Asp Val Thr Val Thr Trp Glu Val Asp
                165                 170                 175

Gly Thr Thr Gln Thr Thr Gly Ile Glu Asn Ser Lys Thr Pro Gln Asn
            180                 185                 190

Ser Ala Asp Cys Thr Tyr Asn Leu Ser Ser Thr Leu Thr Leu Thr Ser
        195                 200                 205

Thr Gln Tyr Asn Ser His Lys Glu Tyr Thr Cys Lys Val Thr Gln Gly
    210                 215                 220

Thr Thr Ser Val Val Gln Ser Phe Asn Arg Gly Asp Cys
225                 230                 235

<210> SEQ ID NO 16
<211> LENGTH: 456
<212> TYPE: PRT
<213> ORGANISM: Artificial Sequence
<220> FEATURE:
<223> OTHER INFORMATION: SYNTHESIZED

<400> SEQUENCE: 16

Met Glu Thr Gly Leu Arg Trp Leu Leu Leu Val Ala Val Leu Lys Gly
1               5                   10                  15

Val Gln Cys Gln Ser Leu Glu Glu Ser Gly Gly Arg Leu Val Thr Pro
            20                  25                  30

Gly Gly Ser Leu Thr Leu Thr Cys Thr Ala Ser Gly Leu Thr Ile Asn
        35                  40                  45

Asn Tyr Tyr Ile Ile Trp Val Arg Gln Ala Pro Gly Lys Gly Leu Lys
```

```
            50                  55                  60
Tyr Ile Gly Ile Thr Tyr Gly Gly Phe Ala Tyr Ala Ser Trp
 65                  70                  75                  80

Ala Lys Gly Arg Phe Thr Ile Ser Arg Thr Ser Thr Val Asp Leu
                     85                  90                  95

Lys Met Thr Ser Leu Thr Ala Glu Asp Thr Ala Thr Tyr Phe Cys Val
                    100                 105                 110

Arg Ala Ala Ala Gly Gly Ala Tyr Asp Leu Trp Gly Gln Gly Thr Leu
                115                 120                 125

Val Thr Val Ser Ser Gly Gln Pro Lys Ala Pro Ser Val Phe Pro Leu
        130                 135                 140

Ala Pro Cys Cys Gly Asp Thr Pro Ser Ser Thr Val Thr Leu Gly Cys
145                 150                 155                 160

Leu Val Lys Gly Tyr Leu Pro Glu Pro Val Thr Val Thr Trp Asn Ser
                    165                 170                 175

Gly Thr Leu Thr Asn Gly Val Arg Thr Phe Pro Ser Val Arg Gln Ser
                180                 185                 190

Ser Gly Leu Tyr Ser Leu Ser Ser Val Val Ser Val Thr Ser Ser Ser
            195                 200                 205

Gln Pro Val Thr Cys Asn Val Ala His Pro Ala Thr Asn Thr Lys Val
    210                 215                 220

Asp Lys Thr Val Ala Pro Ser Thr Cys Ser Lys Pro Thr Cys Pro Pro
225                 230                 235                 240

Pro Glu Leu Leu Gly Gly Pro Ser Val Phe Ile Phe Pro Pro Lys Pro
                    245                 250                 255

Lys Asp Thr Leu Met Ile Ser Arg Thr Pro Glu Val Thr Cys Val Val
                260                 265                 270

Val Asp Val Ser Gln Asp Asp Pro Glu Val Gln Phe Thr Trp Tyr Ile
            275                 280                 285

Asn Asn Glu Gln Val Arg Thr Ala Arg Pro Pro Leu Arg Glu Gln Gln
        290                 295                 300

Phe Asn Ser Thr Ile Arg Val Val Ser Thr Leu Pro Ile Ala His Gln
305                 310                 315                 320

Asp Trp Leu Arg Gly Lys Glu Phe Lys Cys Lys Val His Asn Lys Ala
                    325                 330                 335

Leu Pro Ala Pro Ile Glu Lys Thr Ile Ser Lys Ala Arg Gly Gln Pro
                340                 345                 350

Leu Glu Pro Lys Val Tyr Thr Met Gly Pro Pro Arg Glu Glu Leu Ser
            355                 360                 365

Ser Arg Ser Val Ser Leu Thr Cys Met Ile Asn Gly Phe Tyr Pro Ser
    370                 375                 380

Asp Ile Ser Val Glu Trp Glu Lys Asn Gly Lys Ala Glu Asp Asn Tyr
385                 390                 395                 400

Lys Thr Thr Pro Ala Val Leu Asp Ser Asp Gly Ser Tyr Phe Leu Tyr
                    405                 410                 415

Ser Lys Leu Ser Val Pro Thr Ser Glu Trp Gln Arg Gly Asp Val Phe
                420                 425                 430

Thr Cys Ser Val Met His Glu Ala Leu His Asn His Tyr Thr Gln Lys
            435                 440                 445

Ser Ile Ser Arg Ser Pro Gly Lys
    450                 455

<210> SEQ ID NO 17
```

```
<211> LENGTH: 714
<212> TYPE: DNA
<213> ORGANISM: Artificial Sequence
<220> FEATURE:
<223> OTHER INFORMATION: SYNTHESIZED

<400> SEQUENCE: 17
atggacacga gggcccccac tcagctgctg gggctcctgc tgctctggct cccaggtgcc      60
acatttgccc tggtgatgac ccagactcca tcctccgtgc ctgccgctgt gggaggcaca     120
gtcaccatcg gttgccaggc cagtcagagt attagtaggc aagtatcctg gtatcagcag     180
aaaccagggc agcctcccaa gctcctgatc tacagggcat ccactctggc atctggggtc     240
tcatcgcggt tcaaaggcag tggatctggg acagagttca ctctcactat tagcggcgtc     300
cagtgtgacg atgctgccac ttactactgt ctaggtattg ttactgaccg tattgctgat     360
gggcttgctt tcggcggagg gaccgaggtg gtggtcaaag gtgatccagt tgcacctact     420
gtcctcatct tcccaccagc tgctgatcag gtggcaactg gaacagtcac catcgtgtgt     480
gtggcgaata aatactttcc cgatgtcacc gtcacctggg aggtggatgg caccacccaa     540
acaactggca tcgagaacag taaaacaccg cagaattctg cagattgtac ctacaacctc     600
agcagcactc tgacactgac cagcacacag tacaacagcc acaaagagta cacctgcaag     660
gtgacccagg gcacgacctc agtcgtccag agcttcaata ggggtgactg ttag           714

<210> SEQ ID NO 18
<211> LENGTH: 1371
<212> TYPE: DNA
<213> ORGANISM: Artificial Sequence
<220> FEATURE:
<223> OTHER INFORMATION: SYNTHESIZED

<400> SEQUENCE: 18
atggagactg ggctgcgctg gcttctcctg gtcgctgtgc tcaaaggtgt ccagtgtcag      60
tcggtggagt cagtccggggg tcgcctagtc acgcctggga caccctgac actcacctgc     120
acagtctctg gattcagcat caatgcctat ggaattaact gggtccgcca ggctccaggg     180
aaggggctgg aatacatcgg attcagtgct cctcataccg catcctacgc gaggtggaca     240
aagggccgat tcaccatgtc cagaacctcg accacggtgg atctgagaat gaccagccca     300
acaaccgagg acacgccac ctacttttgt gccagatatg atcggggtgg gatggtattt     360
aacttgtggg gccaaggcac cctggtcacc gtctcctcag gcaacctaa ggctccatca     420
gtcttcccac tggccccctg ctgcgggac acacccagct ccacggtgac cctgggctgc     480
ctggtcaaag ggtacctccc ggagccagtg accgtgacct ggaactcggg caccctcacc     540
aatggggtac gcaccttccc gtccgtccgg cagtcctcag gcctctactc gctgagcagc     600
gtggtgagcg tgacctcaag cagccagccc gtcacctgca acgtggccca cccagccacc     660
aacaccaaag tggacaagac cgttgcgccc tcgacatgca gcaagcccac gtgcccaccc     720
cctgaactcc tggggggacc gtctgtcttc atcttccccc caaaacccaa ggacaccctc     780
atgatctcac gcacccccga ggtcacatgc gtggtggtgg acgtgagcca ggatgacccc     840
gaggtgcagt tcatggtca cataaacaac gagcaggtgc gcaccgcccg gccgccgcta     900
cgggagcagc agttcaacag cacgatccgc gtggtcagca ccctccccat cgcgcaccag     960
gactggctga ggggcaagga gttcaagtgc aaagtccaca acaaggcact cccggcccc    1020
atcgagaaaa ccatctccaa agccagaggg cagcccctgg agccgaaggt ctacaccatg    1080
ggccctcccc gggaggagct gagcagcagg tcggtcagcc tgacctgcat gatcaacggc    1140
```

| | |
|---|---:|
| ttctacccett ccgacatctc ggtggagtgg gagaagaacg ggaaggcaga ggacaactac | 1200 |
| aagaccacgc cggccgtgct ggacagcgac ggctcctact tcctctacag caagctctca | 1260 |
| gtgcccacga gtgagtggca gcggggcgac gtcttcacct gctccgtgat gcacgaggcc | 1320 |
| ttgcacaacc actacacgca gaagtccatc tcccgctctc cgggtaaatg a | 1371 |

<210> SEQ ID NO 19
<211> LENGTH: 714
<212> TYPE: DNA
<213> ORGANISM: Artificial Sequence
<220> FEATURE:
<223> OTHER INFORMATION: SYNTHESIZED

<400> SEQUENCE: 19

| | |
|---|---:|
| atggacacga gggcccccac tcagctgctg gggctcctgc tgctctggct cccaggtgcc | 60 |
| acatttgcca ttgaaatgac ccagactcca tcccctgtgt ctgcagttgt gggaggcaca | 120 |
| gtcaccatca attgtcagtc cagtcagaac gttttttcgta agaactattt atcctggttt | 180 |
| cagcagaaac cagggcagcc tcccaagctc ctgatcagtt atatagacag tctgacatct | 240 |
| ggggtcccat cgcgattcag cggcagtgga gctgggacac agttcactct caccatcagt | 300 |
| gacgtgcagt gtgacgatgc tgccacttat tactgtttag cgttgatgg tagtgctaat | 360 |
| gatgctactt cggcggagg gaccgaggtg gtggtcgaag tgatccagt tgcacctact | 420 |
| gtcctcatct tcccaccagc tgctgatcag gtggcaactg gaacagtcac catcgtgtgt | 480 |
| gtggcgaata atactttcc cgatgtcacc gtcacctggg aggtggatgg caccacccaa | 540 |
| acaactggca tcgagaacag taaaacaccg cagaattctg cagattgtac ctacaacctc | 600 |
| agcagcactc tgacactgac cagcacacag tacaacagcc acaaagagta cacctgcaag | 660 |
| gtgacccagg gcacgacctc agtcgtccag agcttcaata ggggtgactg ttag | 714 |

<210> SEQ ID NO 20
<211> LENGTH: 1371
<212> TYPE: DNA
<213> ORGANISM: Artificial Sequence
<220> FEATURE:
<223> OTHER INFORMATION: SYNTHESIZED

<400> SEQUENCE: 20

| | |
|---|---:|
| atggagactg ggctgcgctg gcttctcctg gtcgctgtgc tcaaaggtgt ccagtgtcag | 60 |
| tcgctggagg agtccggggg tcgcctggta cgcctggag atccctgac actcacctgc | 120 |
| acagcctctg gactcaccat caataactac tacataattt gggtccgcca ggctccagga | 180 |
| aaggggctga atacatcgg aatcacctat ggtggtggtt ttgcatacta cgcgagctgg | 240 |
| gcgaaaggcc gattcaccat ctccagaacc tcgaccacgg tggatctgaa aatgaccagt | 300 |
| ctgacagccg aggacacggc cacttatttc tgtgtcagag ctgcggctgg tggtgcttat | 360 |
| gatttgtggg gccaaggcac cctggtcacc gtctcctcag gcaacctaa ggctccatca | 420 |
| gtcttcccac tggccccctg ctgcgggac acacccagct ccacggtgac cctgggctgc | 480 |
| ctggtcaaag ggtacctccc ggagccagtg accgtgacct ggaactcggg caccctcacc | 540 |
| aatgggggtac gcaccttccc gtccgtcgg cagtcctcag gcctctactc gctgagcagc | 600 |
| gtggtgagcg tgacctcaag cagccagccc gtcacctgca acgtggccca cccagccacc | 660 |
| aacaccaaag tggacaagac cgttgcgccc tcgacatgca gcagccccac gtgcccaccc | 720 |
| cctgaactcc tggggggacc gtctgtcttc atcttccccc caaaacccaa ggacaccctc | 780 |

```
atgatctcac gcaccccga ggtcacatgc gtggtggtgg acgtgagcca ggatgacccc        840
gaggtgcagt tcacatggta cataaacaac gagcaggtgc gcaccgcccg ccgccgccta        900
cgggagcagc agttcaacag cacgatccgc gtggtcagca ccctccccat cgcgcaccag        960
gactggctga ggggcaagga gttcaagtgc aaagtccaca acaaggcact cccggccccc       1020
atcgagaaaa ccatctccaa agccagaggg cagcccctgg agccgaaggt ctacaccatg       1080
ggccctcccc gggaggagct gagcagcagg tcggtcagcc tgacctgcat gatcaacggc       1140
ttctacccct tccgacatctc ggtggagtgg gagaagaacg ggaaggcaga ggacaactac       1200
aagaccacgc cggccgtgct ggacagcgac ggctcctact cctctacag caagctctca       1260 gtgcccacga gtgagtggca gcggggcgac gtcttcacct gctccgtgat gcacgaggcc       1320 tgcacaacc actacacgca gaagtccatc tcccgctctc cgggtaaatg a                 1371
```

<210> SEQ ID NO 21
<211> LENGTH: 8
<212> TYPE: PRT
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa is a polar amino acid selected from the
      group consisting of serine, threonine, asparagine, and glutamine
<220> FEATURE:
<221> NAME/KEY: MISC_FEATURE
<222> LOCATION: (6)..(6)
<223> OTHER INFORMATION: Xaa is a hydrophobic amino acid selected from
      the group consisting of alanine, valine, isoleucine, leucine,
      methionine, phenylalanine, tyrosine and tryptophan
<220> FEATURE:
<221> NAME/KEY: misc_feature
<222> LOCATION: (7)..(7)
<223> OTHER INFORMATION: Xaa can be any naturally occurring amino acid

<400> SEQUENCE: 21

Gln Xaa Ser Gln Xaa Xaa Xaa Arg
1               5

<210> SEQ ID NO 22
<211> LENGTH: 7
<212> TYPE: PRT
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: Xaa is a hydrophobic amino acid selected from
      the group consisting of alanine, valine, isoleucine, leucine,
      methionine, phenylalanine, tyrosine and tryptophan
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa is a polar amino acid selected from the
      group consisting of serine, threonine, asparagine, and glutamine
<220> FEATURE:

```
<221> NAME/KEY: misc_feature
<222> LOCATION: (6)..(6)
<223> OTHER INFORMATION: Xaa can be any naturally occurring amino acid

<400> SEQUENCE: 22

Xaa Xaa Xaa Xaa Leu Xaa Ser
1               5

<210> SEQ ID NO 23
<211> LENGTH: 9
<212> TYPE: PRT
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 23

Ala Xaa Tyr Ala Xaa Trp Xaa Lys Gly
1               5

<210> SEQ ID NO 24
<211> LENGTH: 9
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa is a hydrophobic amino acid selected from
      the group consisting of alanine, valine, isoleucine, leucine,
      methionine, phenylalanine, tyrosine and tryptophan
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
<222> LOCATION: (6)..(7)
<223> OTHER INFORMATION: Xaa is a hydrophobic amino acid selected from
      the group consisting of alanine, valine, isoleucine, leucine,
      methionine, phenylalanine, tyrosine and tryptophan
<220> FEATURE:
<221> NAME/KEY: misc_feature
<222> LOCATION: (8)..(9)
<223> OTHER INFORMATION: Xaa can be any naturally occurring amino acid

<400> SEQUENCE: 24

Xaa Xaa Xaa Gly Gly Xaa Xaa Xaa Xaa
1               5
```

ANTI-ACETAMINOPHEN ANTIBODIES AND ACETAMINOPHEN PROTEIN ADDUCTS

CROSS REFERENCE TO RELATED APPLICATIONS

This application claims the benefit of U.S. patent application Ser. No. 15/532,418, filed Jun. 1, 2017, which claims the benefit of International Patent Application number PCT/US2015/063786, filed Dec. 3, 2015 which claims the benefit of U.S. Provisional Application No. 62/086,923, filed Dec. 3, 2014, the disclosures of which are hereby incorporated by reference in their entirety.

GOVERNMENTAL RIGHTS

This invention was made with government support under R42 DK079387-03 awarded by the NIH. The government has certain rights in the invention.

FIELD OF THE INVENTION

The present disclosure provides isolated antibodies that bind to acetaminophen-protein adducts that are useful in the detection and diagnosis of acetaminophen-induced toxicity.

BACKGROUND OF THE INVENTION

Acetaminophen (APAP) is the most common pharmaceutical product associated with drug toxicity. In severe cases, APAP overdose may lead to acute liver failure (ALF) and death. Over 100,000 telephone calls concerning APAP overdose are made to poison control centers in the U.S. annually. The FDA estimates that approximately 450 deaths are related to APAP overdose annually. For patients that seek treatment within 24 hours of an APAP overdose, and are able to provide accurate information regarding the time and amount of APAP ingested, APAP overdose is relatively straightforward to diagnose and treat. However, current methods of diagnosing APAP overdose, such as the Rumack nomogram, are not very useful to diagnose patients after 24 hours of an APAP overdose, when information regarding time and dose of APAP ingested is not available, or patients that use alcohol, chronically ingest supratherapeutic doses of APAP, or use sustained release APAP formulations. Other laboratory tests, such as serum alanine aminotransferase (ALT) and serum aspartate aminotransferase (AST), indicate the occurrence of liver damage, but neither bioindicator is specific to APAP overdose.

Accordingly, a need exists in the art for a method of accurately diagnosing APAP toxicity, including occult APAP poisoning, even 24 hours or longer after the overdose.

SUMMARY OF THE INVENTION

In an aspect, the disclosure provides an isolated antibody that specifically binds an acetaminophen-protein adduct but does not specifically bind free acetaminophen and recognizes the immunogen: Carrier Protein-2-iminothiolane-APAP.

In another aspect, the disclosure provides an isolated antibody that specifically binds an acetaminophen-protein adduct but does not specifically bind free acetaminophen and comprises a heavy chain CDR3 comprising the amino acid sequence of SEQ ID NO:6 with zero to two amino acid substitutions or SEQ ID NO:12 with zero to two amino acid substitutions.

In still another aspect, the disclosure provides an isolated antibody that specifically binds acetaminophen-protein adduct but does not specifically bind free acetaminophen and comprises a light chain CDR3 comprising the amino acid sequence of SEQ ID NO:3 with zero to two amino acid substitutions or SEQ ID NO:9 with zero to two amino acid substitutions.

In still yet another aspect, the disclosure provides an isolated antibody that specifically binds acetaminophen-protein adduct but does not specifically bind free acetaminophen and comprises a light chain CDR3 comprising the amino acid sequence of Leu-Gly-h and/or a heavy chain CDR3 comprising the amino acid sequence of SEQ ID NO:24, wherein h is a hydrophobic amino acid selected from the group consisting of alanine, valine, isoleucine, leucine, methionine, phenylalanine, tyrosine and tryptophan.

In yet another aspect, the disclosure provides a method for measuring the amount of acetaminophen-protein adduct in a biological sample. The method comprises measuring the amount of acetaminophen-protein adduct in a biological sample obtained from a subject by immunoassay comprising at least one isolated antibody that specifically binds acetaminophen-protein adduct but does not specifically bind free acetaminophen, wherein the antibody comprises an amino acid sequence selected from the group consisting of SEQ ID NO: 1-12 with zero to two amino acid substitutions or wherein the antibody specifically binds to an acetaminophen protein adduct about 2000 times more effectively than free acetaminophen.

In a different aspect, the disclosure provides a method for detecting acetaminophen-induced toxicity in a subject. The method comprises (i) measuring the amount of acetaminophen-protein adduct in a biological sample obtained from a subject by immunoassay using at least one isolated antibody that specifically binds acetaminophen-protein adduct but does not specifically bind free acetaminophen, wherein the antibody comprises an amino acid sequence selected from the group consisting of SEQ ID NO: 1-12 with zero to two amino acid substitutions or wherein the antibody specifically binds to an acetaminophen protein adduct about 2000 times more effectively than free acetaminophen; and (ii) comparing the amount of acetaminophen-protein adduct in the sample to a reference value, wherein a greater amount of acetaminophen-protein adduct in the sample compared to the reference value indicates acetaminophen-induced toxicity in the subject.

In other aspects, the disclosure provides a method to determine if hepatotoxicity in a subject is due to acetaminophen-induced toxicity. The method comprises (i) measuring the presence of and/or amount of acetaminophen-protein adduct in a biological sample obtained from a subject by immunoassay using at least one isolated antibody that specifically binds acetaminophen-protein adduct but does not specifically bind free acetaminophen, wherein the antibody comprises an amino acid sequence selected from the group consisting of SEQ ID NO: 1-12 with zero to two amino acid substitutions or wherein the antibody specifically binds to an acetaminophen protein adduct about 2000 times more effectively than free acetaminophen; and (ii) determining if acetaminophen-protein adduct is present, wherein if acetaminophen-protein adduct is not present, the hepatotoxicity in the subject is not due to acetaminophen-induced toxicity and wherein if acetaminophen-protein adduct is present, comparing the amount of acetaminophen-protein adduct in the sample to a reference value, wherein a greater amount of acetaminophen-protein adduct in the sample compared to the reference value indicates the hepatotoxicity in the subject is due to acetaminophen-induced toxicity.

In certain aspects, the disclosure provides a method of producing a monoclonal antibody with specificity for an acetaminophen-protein adduct. The method comprises immunizing a subject with an immunogen comprising Carrier Protein-2-iminothiolane-APAP.

BRIEF DESCRIPTION OF THE FIGURES

The application file contains at least one drawing executed in color. Copies of this patent application publication with color drawing(s) will be provided by the Office upon request and payment of the necessary fee.

DETAILED DESCRIPTION OF THE INVENTION

Figure 1:
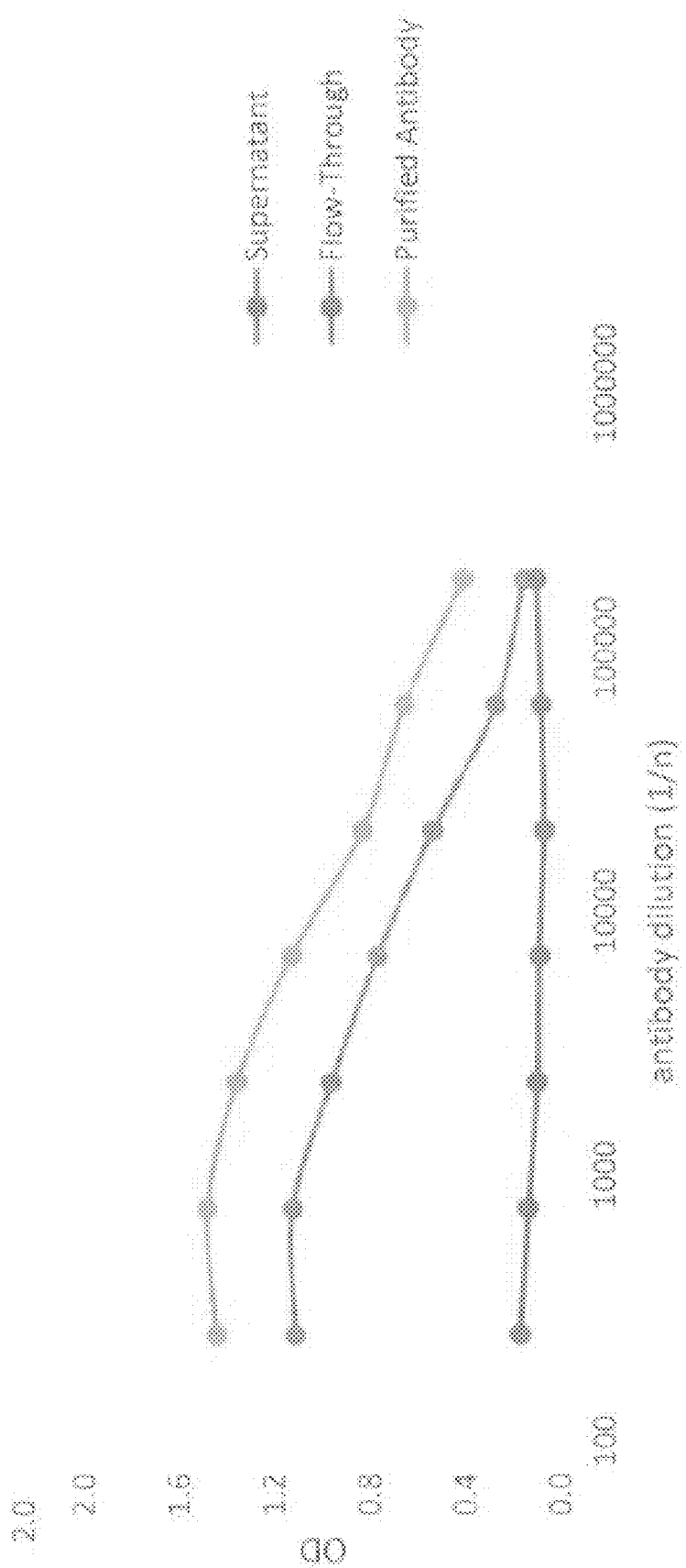
FIG. 1 depicts an ELISA assay showing binding of antibody 14-12 to antigen ATD-1.

The disclosure provides antibodies that react specifically with acetaminophen-protein adducts that are formed physiologically during the pathogenesis of acetaminophen-mediated toxicity. Antibodies of the invention do not react specifically with free acetaminophen.

The disclosure also provides methods of use of the antibodies of the invention. Antibodies of the invention may be used to detect acetaminophen-protein adducts in a biological sample or diagnose acetaminophen-mediated toxicity in a subject.

Additionally, the disclosure provides a novel immunogen for the purpose of preparing antibodies with specificity for acetaminophen protein adducts. Specifically, the immunogen is Carrier Protein-2-iminothiolane linked-acetaminophen. The novel immunogen was prepared by modifying an immunogenic carrier protein (CP) with 2-iminothiolane (2-IT) to provide a highly substituted CP with numerous 5-carbon linker molecules with terminal sulfhydryl groups. This 2-IT modified CP was then covalently modified at the terminal sulfhydryl groups by reaction with synthetically prepared N-acetyl-p-benzoquinone imine.

I. Antibodies

Acetaminophen (APAP)-induced toxicity is mediated by covalent binding of the reactive metabolite N-acetyl-p-benzoquinone imine (NAPQI) to essential proteins in the liver. At therapeutic doses, the metabolite is effectively detoxified by conjugation with glutathione to form a 3-(glutathion-S-yl)acetaminophen conjugate. After overdose, this reaction depletes the liver of glutathione, and the metabolite covalently binds to hepatic proteins. The major adduct formed in this scenario is the acetaminophen-cysteine adduct, 3-(cystein-S-yl)acetaminophen. Anti-acetaminophen-protein adduct antibodies of the disclosure include antibodies that bind protein adducts of acetaminophen.

As noted above, acetaminophen can form protein adducts by conjugation with amino acids. Anti-acetaminophen-protein adduct antibodies of the disclosure include antibodies that bind to one or more acetaminophen-protein adducts. Specifically, an acetaminophen-protein adduct antibody of the disclosure binds to an acetaminophen modified cysteine in the polypeptide chain of any adducted protein. In some embodiments, an anti-acetaminophen-protein adduct antibody binds a 3-(cystein-S-yl)acetaminophen-protein adduct. In other embodiments, an anti-acetaminophen-protein adduct antibody binds a 3-(glutathion-S-yl)acetaminophen-protein adduct. In different embodiments, an anti-acetaminophen-protein adduct antibody binds acetaminophen mercapturate. In other embodiments, an anti-acetaminophen-protein adduct antibody binds to an acetaminophen protein adduct on a protein modified by NAPQI. Any protein with an exposed cysteine sulfhydryl is a candidate for reaction with NAPQI and resultant formation of the 3-(cystein-S-yl)acetaminophen-protein adduct. Non-limiting examples of proteins modified by NAPQI include betaine-homocysteine S-methyltransferase 1 (BHMT), cytoplasmic aspartate aminotransferase (cAspAT), 1,4-alpha-glucan-branching enzyme, formimidoyltransferase-cyclodeaminase (FTCD), dystrophin, aldehyde dehydrogenase, ATP synthase alpha-chain mitochondrial, calregulin, carbamoylphosphate synthetase I, carbonate dehydratase III (CA-III), aldehyde dehydrogenase (AHD-M1), glutamate dehydrogenase (GDH), glutamate-ammonia ligase, cellular glutathione peroxidase, glutathione transferases (GST), glutathione S-transferase P 1, GAPDH, AdoMet synthetase 1, macrophage 23 kDa stress protein, eIF-4A-I, 56 kDa acetaminophen-binding protein, L-iditol 2-dehydrogenase, amine N-methyltransferase, antioxidant protein 1, tropomyosin 3, urate oxidase, 10-formyltetrahydrofolate dehydrogenase, hemoglobin, 56 kDa selenium-binding protein, lamin A, cellular thyroid hormone binding protein, 58 kDa microsomal protein, Life Tech mouse embryo 8 5dpc 10664019 *Mus musculus* cDNA clone, inorganic pyrophosphatase, NML *Mus musculus* cDNA clone, 2-4-dienoyl-CoA reductase mitochondrial, 3-HAI,3-hydroxyanthranilate 3-4-dioxygenase, 94 kDa glucose-regulated protein, cytosolic inhibitor of Nrf2, serum albumin, and delayed early response protein 6.

In all instances, an antibody of the disclosure specifically binds one or more acetaminophen-protein adducts but does not specifically bind free acetaminophen. Accordingly, an antibody of the disclosure binds acetaminophen-protein adduct more effectively than free acetaminophen. For example, an acetaminophen-protein adduct antibody binds to an acetaminophen protein about 100, about 250, about 500, about 1000, about 1500, about 2000, about 2500, about 3000, about 3500, about 4000, about 4500, about 5000, about 5500, about 6000, about 6500, about 7000, about 7500, about 8000, about 8500, about 9000, about 9500 or about 10,000 times more effectively than free acetaminophen. Additionally, an acetaminophen-protein adduct antibody binds to an acetaminophen protein adduct about 1000 to about 2000, about 2000 to about 3000, about 3000 to about 4000, about 4000 to about 5000, about 5000 to about 6000, about 6000 to about 7000, about 7000 to about 8000, or about 8000 to about 9000 times more effectively than free acetaminophen. In one embodiment, an acetaminophen-protein adduct antibody binds to an acetaminophen protein about 2000 times more effectively than free acetaminophen. In another embodiment, an acetaminophen-protein adduct antibody binds to an acetaminophen protein about 8000 times more effectively than free acetaminophen. The phrase "specifically binds" herein means antibodies bind to the acetaminophen-protein adduct with an affinity constant or Affinity of interaction (KD) in the range of 0.1 pM to 10 nM, with a preferred range being 0.1 pM to 1 nM. Methods of determining whether an antibody binds to acetaminophen protein adducts are known in the art. In certain embodiments, the specific antibodies may recognize an acetaminophen modified cysteine in the polypeptide chain of any adducted protein. In some embodiments, the specific antibodies may recognize a 3-(cystein-S-yl)acetaminophen-protein adduct. In other embodiments, the specific antibodies may recognize a 3-(glutathion-S-yl)acetaminophen-protein adduct. In still other embodiments, the antibodies may recognize an acetaminophen mercapturate.

Anti-acetaminophen-protein adduct antibodies useful herein also include all antibodies that specifically bind acetaminophen protein adducts in a biological sample. In an exemplary embodiment, anti-acetaminophen-protein adduct antibodies useful herein include all antibodies that specifically bind 3-(cystein-S-yl)acetaminophen present in a biological sample.

In an aspect, antibodies useful herein include those antibodies which have been isolated, characterized, purified, are functional and have been recovered (obtained) for use in an assay to detect acetaminophen-protein adduct in a biological sample obtained from a living subject and predict the development of acetaminophen toxicity in the subject. In another aspect, antibodies useful herein include those antibodies which have been isolated, characterized, purified, are functional and have been recovered (obtained) for use in an assay to detect acetaminophen-protein adduct in a biological sample obtained from a living subject and diagnose the development of acetaminophen toxicity in the subject. In another aspect, antibodies useful herein include those antibodies which have been isolated, characterized, purified, are functional and have been recovered (obtained) or for use in an assay to detect acetaminophen-protein adduct in a biological sample obtained from a living subject and classify the subject as having an increased risk of developing acetaminophen toxicity in the subject's lifetime. In another aspect, antibodies useful herein include those antibodies which have been isolated, characterized, purified, are functional and have been recovered (obtained) for use and are listed in Table A, as well as variants thereof (e.g. humanized forms, chimeric forms, and immunological fragments).

TABLE A

Antibodies of the invention

| Antibody Name | Immunogen |
|---|---|
| 14-12 | CP-2IT-APAP |
| 14-7 | CP-2IT-APAP |
| 22-8 | CP-2IT-APAP |

The term "antibody" includes the term "monoclonal antibody". "Monoclonal antibody" refers to an antibody that is derived from a single copy or clone, including e.g., any eukaryotic, prokaryotic, or phage clone. "Monoclonal antibody" is not limited to antibodies produced through hybridoma technology. Monoclonal antibodies can be produced using e.g., hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

Further by "antibody" is meant a functional monoclonal antibody, or an immunologically effective fragment thereof; such as an Fab, Fab', or F(ab')2 fragment thereof. In some contexts herein, fragments will be mentioned specifically for emphasis; nevertheless, it will be understood that regardless of whether fragments are specified, the term "antibody" includes such fragments as well as single-chain forms. As long as the protein retains the ability specifically to bind its intended target, it is included within the term "antibody." Also included within the definition "antibody" for example are single chain forms, generally designated Fv regions, of antibodies with this specificity. Optionally, the antibodies useful in the discovery are produced recombinantly, as manipulation of the typically rabbit or other non-human antibodies with the appropriate specificity is required in order to convert them to humanized form. Antibodies may or may not be glycosylated. Antibodies are properly cross-linked via disulfide bonds, as is known.

The basic antibody unit of an antibody useful herein comprises a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function.

Anti-acetaminophen-protein adduct antibodies useful herein include those which are isolated, characterized, purified, function and have been recovered (obtained) from a process for their preparation and thus available for use herein in a useful form in a diagnostically sufficient amount.

Light chains are classified as kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids.

The variable regions of each light/heavy chain pair form the antibody binding site. Thus, an intact antibody has two binding sites. The chains exhibit the same general structure of relatively conserved framework regions (FR) joined by three hypervariable regions, also called complementarily determining regions (hereinafter referred to as "CDRs.") The CDRs from the two chains are aligned by the framework regions, enabling binding to a specific epitope. From N-terminal to C-terminal, both light and heavy chains comprise the domains FR1, CDR1, FR2, CDR2, FR3, CDR3 and FR4 respectively. The assignment of amino acids to each domain is in accordance with known conventions (See, Kabat "Sequences of Proteins of Immunological Interest" National Institutes of Health, Bethesda, Md., 1987 and 1991; Chothia, et al, J. Mol. Bio. (1987) 196:901-917; Chothia, et al., Nature (1989) 342:878-883).

In an aspect, monoclonal anti-acetaminophen-protein adduct antibodies are generated with appropriate specificity by standard techniques of immunization of mammals, forming hybridomas from the antibody-producing cells of said mammals or otherwise immortalizing them, and culturing the hybridomas or immortalized cells to assess them for the appropriate specificity. In the present case, such antibodies could be generated by immunizing a human, rabbit, rat or mouse, for example, with an immunogen as described in Section III. Materials for recombinant manipulation can be obtained by retrieving the nucleotide sequences encoding the desired antibody from the hybridoma or other cell that produces it. These nucleotide sequences can then be manipulated and isolated, characterized, purified and, recovered for use herein.

In an embodiment, an antibody of the invention may be humanized. As used herein "humanized antibody" includes an anti-acetaminophen antibody that is composed partially or fully of amino acid sequences derived from a human antibody germline by altering the sequence of an antibody having non-human complementarity determining regions ("CDR"). The simplest such alteration may consist simply of substituting the constant region of a human antibody for the murine or rabbit constant region, thus resulting in a human/murine or rabbit chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. CDRs may also be randomly mutated such that binding activity and affinity for acetaminophen protein adduct is maintained or enhanced in the context of fully human germline framework regions or framework regions that are substantially human. Substantially human frameworks have at least 90%, 95%, or 99% sequence identity with a known human framework sequence. Fully useful human antibodies may also be produced in genetically modified mice whose immune systems have been altered to correspond to human immune systems. As mentioned above, it is sufficient for use in the methods of this discovery, to employ an immunologically specific fragment of the antibody, including fragments representing single chain forms.

The antibodies of the present invention may also be used as fusion proteins known as single chain variable fragments (scFv). These scFvs are comprised of the heavy and light chain variable regions connected by a linker. In most instances, but not all, the linker may be a peptide. A linker peptide is preferably from about 10 to 25 amino acids in length. Preferably, a linker peptide is rich in glycine, as well as serine or threonine. ScFvs can be used to facilitate phage display or can be used for flow cytometry, immunohistochemistry, or as targeting domains. Methods of making and using scFvs are known in the art.

In a preferred embodiment, the scFvs of the present invention are conjugated to a human constant domain. In some embodiments, the heavy constant domain is derived from an IgG domain, such as IgG1, IgG2, IgG3, or IgG4. In other embodiments, the heavy chain constant domain may be derived from IgA, IgM, or IgE.

A preferred antibody is a rabbit antibody derived from a hybridoma designated 14-12, 14-7 or 22-8. As used herein, the term "derived from" means that the "derived" antibody comprises at least one CDR region from the antibody produced by 14-12, 14-7 or 22-8. Stated another way, the "derived antibody" comprises at least one CDR region comprised of the amino acid sequence selected from the group consisting of SEQ ID NO: 1, 2, 3, 4, 5, 6, 7, 8, 9, 10, 11, and 12.

In one embodiment, an antibody of the invention may be derived from the hybridoma 14-12 or 14-7, and may be encoded by a nucleic acid sequence comprising 90, 91, 92, 93, 94, 95, 96, 97, 98, or 99% identity to the light chain variable region of SEQ ID NO:17, or may be encoded by a nucleic acid sequence comprising 90, 91, 92, 93, 94, 95, 96, 97, 98, or 99% identity to the heavy chain variable region of SEQ ID NO:18. In another embodiment, an antibody of the invention may be derived from the hybridoma 14-12 or 14-7, and may be encoded by an amino acid sequence comprising 90, 91, 92, 93, 94, 95, 96, 97, 98, or 99% identity to the light chain variable region of SEQ ID NO:13, or may be encoded by a nucleic acid sequence comprising 90, 91, 92, 93, 94, 95, 96, 97, 98, or 99% identity to the heavy chain variable region of SEQ ID NO:14.

In a different embodiment, an antibody of the invention may be derived from the hybridoma 22-8, and may be encoded by a nucleic acid sequence comprising 90, 91, 92, 93, 94, 95, 96, 97, 98, or 99% identity to the light chain variable region of SEQ ID NO:19, or may be encoded by a nucleic acid sequence comprising 90, 91, 92, 93, 94, 95, 96, 97, 98, or 99% identity to the heavy chain variable region of SEQ ID NO:20. In another embodiment, an antibody of the invention may be derived from the hybridoma 22-8, and may be encoded by an amino acid sequence comprising 90, 91, 92, 93, 94, 95, 96, 97, 98, or 99% identity to the light chain variable region of SEQ ID NO:15, or may be encoded by an amino acid sequence comprising 90, 91, 92, 93, 94, 95, 96, 97, 98, or 99% identity to the heavy chain variable region of SEQ ID NO:16.

In an exemplary embodiment of an antibody of the invention that binds to an acetaminophen-protein adduct, the antibody comprises the light chain amino acid sequence of SEQ ID NO:13 and the heavy chain amino acid sequence of SEQ ID NO:14 [i.e. the monoclonal antibody referred to herein as 14-12 or 14-7]. In another exemplary embodiment of an antibody of the invention that binds to an acetaminophen-protein adduct, the antibody comprises the light chain amino acid sequence of SEQ ID NO:15 and the heavy chain amino acid sequence of SEQ ID NO:16 [i.e. the monoclonal antibody referred to herein as 22-8]. In another exemplary embodiment of an antibody of the invention that binds to an acetaminophen-protein adduct, the antibody comprises the light chain nucleic acid sequence of SEQ ID NO:17 and the heavy chain amino acid sequence of SEQ ID NO:18 [i.e. the monoclonal antibody referred to herein as mAb 14-12 or 14-7]. In another exemplary embodiment of an antibody of the invention that binds to an acetaminophen-protein adduct, the antibody comprises the light chain nucleic acid sequence of SEQ ID NO:19 and the heavy chain nucleic acid sequence of SEQ ID NO:20 [i.e. the monoclonal antibody referred to herein as 22-8].

In one embodiment, an antibody of the invention may comprise a light chain CDR1, such as the antibodies 1, 49 and 97 of Table B. In another embodiment, an antibody of the invention may comprise a light chain CDR2, such as the antibodies 4, 52 and 100 of Table B. In yet another embodiment, an antibody of the invention may comprise a light chain CDR3, such as the antibodies 6, 54 and 102 of Table B. In an alternative embodiment, an antibody of the invention may comprise a combination of two or three light chain CDRs, such as the antibodies 2, 3, 5, 50, 51, 53, 98, 99 and 101 of Table B.

Similarly, in one embodiment, an antibody of the invention may comprise a heavy chain CDR1, such as the antibodies 7, 55 and 103 of Table B. In another embodiment, an antibody of the invention may comprise a heavy chain CDR2, such as the antibodies 10, 58 and 106 of Table B. In yet another embodiment, an antibody of the invention may comprise a heavy chain CDR3, such as the antibodies 12, 60 and 108 of Table B. In an alternative embodiment, an antibody of the invention may comprise a combination of two or three heavy chain CDRs, such as the antibodies 8, 9, 11, 56, 57, 59, 104, 105 and 107 of Table B.

Alternatively, an antibody of the invention may comprise one or more light chain CDRs and one or more heavy chain CDRs, such as the antibodies 13-48, 61-96 and 109-144 of Table B.

TABLE B

| Antibody | Light Chain | | | Heavy Chain | | |
|---|---|---|---|---|---|---|
| | CDR1 | CDR2 | CDR3 | CDR1 | CDR2 | CDR3 |
| 1 | SEQ ID NO:1 | | | | | |
| 2 | SEQ ID NO:1 | SEQ ID NO:2 | | | | |
| 3 | SEQ ID NO:1 | SEQ ID NO:2 | SEQ ID NO:3 | | | |
| 4 | | SEQ ID NO:2 | | | | |
| 5 | | SEQ ID NO:2 | SEQ ID NO:3 | | | |
| 6 | | | SEQ ID NO:3 | | | |
| 7 | | | | SEQ ID NO:4 | | |
| 8 | | | | SEQ ID NO:4 | SEQ ID NO:5 | |
| 9 | | | | SEQ ID NO:4 | SEQ ID NO:5 | SEQ ID NO:6 |
| 10 | | | | | SEQ ID NO:5 | |
| 11 | | | | | SEQ ID NO:5 | SEQ ID NO:6 |
| 12 | | | | | | SEQ ID NO:6 |
| 13 | SEQ ID NO:1 | | | SEQ ID NO:4 | | |
| 14 | SEQ ID NO:1 | | | SEQ ID NO:4 | SEQ ID NO:5 | |
| 15 | SEQ ID NO:1 | | | SEQ ID NO:4 | SEQ ID NO:5 | SEQ ID NO:6 |
| 16 | SEQ ID NO:1 | | | | SEQ ID NO:5 | |
| 17 | SEQ ID NO:1 | | | | SEQ ID NO:5 | SEQ ID NO:6 |
| 18 | SEQ ID NO:1 | | | | | SEQ ID NO:6 |
| 19 | SEQ ID NO:1 | SEQ ID NO:2 | | SEQ ID NO:4 | | |
| 20 | SEQ ID NO:1 | SEQ ID NO:2 | | SEQ ID NO:4 | SEQ ID NO:5 | |
| 21 | SEQ ID NO:1 | SEQ ID NO:2 | | SEQ ID NO:4 | SEQ ID NO:5 | SEQ ID NO:6 |
| 22 | SEQ ID NO:1 | SEQ ID NO:2 | | | SEQ ID NO:5 | |
| 23 | SEQ ID NO:1 | SEQ ID NO:2 | | | SEQ ID NO:5 | SEQ ID NO:6 |
| 24 | SEQ ID NO:1 | SEQ ID NO:2 | | | | SEQ ID NO:6 |
| 25 | SEQ ID NO:1 | SEQ ID NO:2 | SEQ ID NO:3 | SEQ ID NO:4 | | |
| 26 | SEQ ID NO:1 | SEQ ID NO:2 | SEQ ID NO:3 | SEQ ID NO:4 | SEQ ID NO:5 | |
| 27 | SEQ ID NO:1 | SEQ ID NO:2 | SEQ ID NO:3 | SEQ ID NO:4 | SEQ ID NO:5 | SEQ ID NO:6 |
| 28 | SEQ ID NO:1 | SEQ ID NO:2 | SEQ ID NO:3 | | SEQ ID NO:5 | |
| 29 | SEQ ID NO:1 | SEQ ID NO:2 | SEQ ID NO:3 | | SEQ ID NO:5 | SEQ ID NO:6 |
| 30 | SEQ ID NO:1 | SEQ ID NO:2 | SEQ ID NO:3 | | | SEQ ID NO:6 |
| 31 | | SEQ ID NO:2 | | SEQ ID NO:4 | | |
| 32 | | SEQ ID NO:2 | | SEQ ID NO:4 | SEQ ID NO:5 | |
| 33 | | SEQ ID NO:2 | | SEQ ID NO:4 | SEQ ID NO:5 | SEQ ID NO:6 |
| 34 | | SEQ ID NO:2 | | | SEQ ID NO:5 | |
| 35 | | SEQ ID NO:2 | | | SEQ ID NO:5 | SEQ ID NO:6 |
| 36 | | SEQ ID NO:2 | | | | SEQ ID NO:6 |
| 37 | | SEQ ID NO:2 | SEQ ID NO:3 | SEQ ID NO:4 | | |
| 38 | | SEQ ID NO:2 | SEQ ID NO:3 | SEQ ID NO:4 | SEQ ID NO:5 | |
| 39 | | SEQ ID NO:2 | SEQ ID NO:3 | SEQ ID NO:4 | SEQ ID NO:5 | SEQ ID NO:6 |
| 40 | | SEQ ID NO:2 | SEQ ID NO:3 | | SEQ ID NO:5 | |
| 41 | | SEQ ID NO:2 | SEQ ID NO:3 | | SEQ ID NO:5 | SEQ ID NO:6 |
| 42 | | SEQ ID NO:2 | SEQ ID NO:3 | | | SEQ ID NO:6 |
| 43 | | | SEQ ID NO:3 | SEQ ID NO:4 | | |
| 44 | | | SEQ ID NO:3 | SEQ ID NO:4 | SEQ ID NO:5 | |
| 45 | | | SEQ ID NO:3 | SEQ ID NO:4 | SEQ ID NO:5 | SEQ ID NO:6 |
| 46 | | | SEQ ID NO:3 | | SEQ ID NO:5 | |
| 47 | | | SEQ ID NO:3 | | SEQ ID NO:5 | SEQ ID NO:6 |
| 48 | | | SEQ ID NO:3 | | | SEQ ID NO:6 |
| 49 | SEQ ID NO:7 | | | | | |
| 50 | SEQ ID NO:7 | SEQ ID NO:8 | | | | |
| 51 | SEQ ID NO:7 | SEQ ID NO:8 | SEQ ID NO:9 | | | |
| 52 | | SEQ ID NO:8 | | | | |
| 53 | | SEQ ID NO:8 | SEQ ID NO:9 | | | |
| 54 | | | SEQ ID NO:9 | | | |
| 55 | | | | SEQ ID NO:10 | | |
| 56 | | | | SEQ ID NO:10 | SEQ ID NO:11 | |
| 57 | | | | SEQ ID NO:10 | SEQ ID NO:11 | SEQ ID NO:12 |
| 58 | | | | | SEQ ID NO:11 | |
| 59 | | | | | SEQ ID NO:11 | SEQ ID NO:12 |
| 60 | | | | | | SEQ ID NO:12 |
| 61 | SEQ ID NO:7 | | | SEQ ID NO:10 | | |
| 62 | SEQ ID NO:7 | | | SEQ ID NO:10 | SEQ ID NO:11 | |
| 63 | SEQ ID NO:7 | | | SEQ ID NO:10 | SEQ ID NO:11 | SEQ ID NO:12 |
| 64 | SEQ ID NO:7 | | | | SEQ ID NO:11 | |
| 65 | SEQ ID NO:7 | | | | SEQ ID NO:11 | SEQ ID NO:12 |
| 66 | SEQ ID NO:7 | | | | | SEQ ID NO:12 |
| 67 | SEQ ID NO:7 | SEQ ID NO:8 | | SEQ ID NO:10 | | |
| 68 | SEQ ID NO:7 | SEQ ID NO:8 | | SEQ ID NO:10 | SEQ ID NO:11 | |

TABLE B-continued

| | Light Chain | | | Heavy Chain | | |
|---|---|---|---|---|---|---|
| Antibody | CDR1 | CDR2 | CDR3 | CDR1 | CDR2 | CDR3 |
| 69 | SEQ ID NO:7 | SEQ ID NO:8 | | SEQ ID NO:10 | SEQ ID NO:11 | SEQ ID NO:12 |
| 70 | SEQ ID NO:7 | SEQ ID NO:8 | | | SEQ ID NO:11 | |
| 71 | SEQ ID NO:7 | SEQ ID NO:8 | | | SEQ ID NO:11 | SEQ ID NO:12 |
| 72 | SEQ ID NO:7 | SEQ ID NO:8 | | | | SEQ ID NO:12 |
| 73 | SEQ ID NO:7 | SEQ ID NO:8 | SEQ ID NO:9 | SEQ ID NO:10 | | |
| 74 | SEQ ID NO:7 | SEQ ID NO:8 | SEQ ID NO:9 | SEQ ID NO:10 | SEQ ID NO:11 | |
| 75 | SEQ ID NO:7 | SEQ ID NO:8 | SEQ ID NO:9 | SEQ ID NO:10 | SEQ ID NO:11 | SEQ ID NO:12 |
| 76 | SEQ ID NO:7 | SEQ ID NO:8 | SEQ ID NO:9 | | SEQ ID NO:11 | |
| 77 | SEQ ID NO:7 | SEQ ID NO:8 | SEQ ID NO:9 | | SEQ ID NO:11 | SEQ ID NO:12 |
| 78 | SEQ ID NO:7 | SEQ ID NO:8 | SEQ ID NO:9 | | | SEQ ID NO:12 |
| 79 | | SEQ ID NO:8 | | SEQ ID NO:10 | | |
| 80 | | SEQ ID NO:8 | | SEQ ID NO:10 | SEQ ID NO:11 | |
| 81 | | SEQ ID NO:8 | | SEQ ID NO:10 | SEQ ID NO:11 | SEQ ID NO:12 |
| 82 | | SEQ ID NO:8 | | | SEQ ID NO:11 | |
| 83 | | SEQ ID NO:8 | | | SEQ ID NO:11 | SEQ ID NO:12 |
| 84 | | SEQ ID NO:8 | | | | SEQ ID NO:12 |
| 85 | | SEQ ID NO:8 | SEQ ID NO:9 | SEQ ID NO:10 | | |
| 86 | | SEQ ID NO:8 | SEQ ID NO:9 | SEQ ID NO:10 | SEQ ID NO:11 | |
| 87 | | SEQ ID NO:8 | SEQ ID NO:9 | SEQ ID NO:10 | SEQ ID NO:11 | SEQ ID NO:12 |
| 88 | | SEQ ID NO:8 | SEQ ID NO:9 | | SEQ ID NO:11 | |
| 89 | | SEQ ID NO:8 | SEQ ID NO:9 | | SEQ ID NO:11 | SEQ ID NO:12 |
| 90 | | SEQ ID NO:8 | SEQ ID NO:9 | | | SEQ ID NO:12 |
| 91 | | | SEQ ID NO:9 | SEQ ID NO:10 | | |
| 92 | | | SEQ ID NO:9 | SEQ ID NO:10 | SEQ ID NO:11 | |
| 93 | SEQ ID NO:9 | SEQ ID NO:10 | SEQ ID NO:11 | SEQ ID NO:12 | | |
| 94 | | | SEQ ID NO:9 | | SEQ ID NO:11 | |
| 95 | | | SEQ ID NO:9 | | SEQ ID NO:11 | SEQ ID NO:12 |
| 96 | | | SEQ ID NO:9 | | | SEQ ID NO:12 |
| 97 | SEQ ID NO:21 | | | | | |
| 98 | SEQ ID NO:21 | SEQ ID NO:22 | | | | |
| 99 | SEQ ID NO:21 | SEQ ID NO:22 | Leu-Gly-h* | | | |
| 100 | | SEQ ID NO:22 | | | | |
| 101 | | SEQ ID NO:22 | Leu-Gly-h* | | | |
| 102 | | | Leu-Gly-h* | | | |
| 103 | | | | Tyr-X-lle** | | |
| 104 | | | | Tyr-X-lle** | SEQ ID NO:23 | |
| 105 | | | | Tyr-X-lle** | SEQ ID NO:23 | SEQ ID NO:24 |
| 106 | | | | | SEQ ID NO:23 | |
| 107 | | | | | SEQ ID NO:23 | SEQ ID NO:24 |
| 108 | | | | | | SEQ ID NO:24 |
| 109 | SEQ ID NO:21 | | | Tyr-X-lle** | | |
| 110 | SEQ ID NO:21 | | | Tyr-X-lle** | SEQ ID NO:23 | |
| 111 | SEQ ID NO:21 | | | Tyr-X-lle** | SEQ ID NO:23 | SEQ ID NO:24 |
| 112 | SEQ ID NO:21 | | | | SEQ ID NO:23 | |
| 113 | SEQ ID NO:21 | | | | SEQ ID NO:23 | SEQ ID NO:24 |
| 114 | SEQ ID NO:21 | | | | | SEQ ID NO:24 |
| 115 | SEQ ID NO:21 | SEQ ID NO:22 | | Tyr-X-lle** | | |
| 116 | SEQ ID NO:21 | SEQ ID NO:22 | | Tyr-X-lle** | SEQ ID NO:23 | |
| 117 | SEQ ID NO:21 | SEQ ID NO:22 | | Tyr-X-lle** | SEQ ID NO:23 | SEQ ID NO:24 |
| 118 | SEQ ID NO:21 | SEQ ID NO:22 | | | SEQ ID NO:23 | |
| 119 | SEQ ID NO:21 | SEQ ID NO:22 | | | SEQ ID NO:23 | SEQ ID NO:24 |
| 120 | SEQ ID NO:21 | SEQ ID NO:22 | | | | SEQ ID NO:24 |
| 121 | SEQ ID NO:21 | SEQ ID NO:22 | Leu-Gly-h* | Tyr-X-lle** | | |
| 122 | SEQ ID NO:21 | SEQ ID NO:22 | Leu-Gly-h* | Tyr-X-lle** | SEQ ID NO:23 | |
| 123 | SEQ ID NO:21 | SEQ ID NO:22 | Leu-Gly-h* | Tyr-X-lle** | SEQ ID NO:23 | SEQ ID NO:24 |
| 124 | SEQ ID NO:21 | SEQ ID NO:22 | Leu-Gly-h* | | SEQ ID NO:23 | |
| 125 | SEQ ID NO:21 | SEQ ID NO:22 | Leu-Gly-h* | | SEQ ID NO:23 | SEQ ID NO:24 |
| 126 | SEQ ID NO:21 | SEQ ID NO:22 | Leu-Gly-h* | | | SEQ ID NO:24 |
| 127 | | SEQ ID NO:22 | | Tyr-X-lle** | | |
| 128 | | SEQ ID NO:22 | | Tyr-X-lle** | SEQ ID NO:23 | |
| 129 | | SEQ ID NO:22 | | Tyr-X-lle** | SEQ ID NO:23 | SEQ ID NO:24 |
| 130 | | SEQ ID NO:22 | | | SEQ ID NO:23 | |
| 131 | | SEQ ID NO:22 | | | SEQ ID NO:23 | SEQ ID NO:24 |
| 132 | | SEQ ID NO:22 | | | | SEQ ID NO:24 |
| 133 | | SEQ ID NO:22 | Leu-Gly-h* | Tyr-X-lle** | | |
| 134 | | SEQ ID NO:22 | Leu-Gly-h* | Tyr-X-lle** | SEQ ID NO:23 | |
| 135 | | SEQ ID NO:22 | Leu-Gly-h* | Tyr-X-lle** | SEQ ID NO:23 | SEQ ID NO:24 |
| 136 | | SEQ ID NO:22 | Leu-Gly-h* | | SEQ ID NO:23 | |
| 137 | | SEQ ID NO:22 | Leu-Gly-h* | | SEQ ID NO:23 | SEQ ID NO:24 |
| 138 | | SEQ ID NO:22 | Leu-Gly-h* | | | SEQ ID NO:24 |
| 139 | | | Leu-Gly-h* | Tyr-X-lle** | | |
| 140 | | | Leu-Gly-h* | Tyr-X-lle** | SEQ ID NO:23 | |
| 141 | | | Leu-Gly-h* | Tyr-X-lle** | SEQ ID NO:23 | SEQ ID NO:24 |
| 142 | | | Leu-Gly-h* | | SEQ ID NO:23 | |

TABLE B-continued

| | Light Chain | | | Heavy Chain | | |
|---|---|---|---|---|---|---|
| Antibody | CDR1 | CDR2 | CDR3 | CDR1 | CDR2 | CDR3 |
| 143 | | | Leu-Gly-h* | | SEQ ID NO:23 | SEQ ID NO:24 |
| 144 | | | Leu-Gly-h* | | | SEQ ID NO:24 |

*wherein h is a hydrophobic amino acid selected from the group consisting of a anine, valine, isoleucine, leucine, methionine, phenylalanine, tyrosine and tryptophan.
* wherein X is any amino acid.

In one embodiment, an antibody of the invention may comprise a light chain variable region comprising a CDR1 of amino acid sequence SEQ ID NO: 1 with zero to two amino acid substitutions, a CDR2 of amino acid sequence SEQ ID NO: 2 with zero to two amino acid substitutions, and a CDR3 of amino acid sequence SEQ ID NO:3 with zero to two amino acid substitutions, or may comprise a heavy chain variable region comprising a CDR1 of amino acid sequence SEQ ID NO: 4 with zero to two amino acid substitutions, a CDR2 of amino acid sequence SEQ ID NO: 5 with zero to two amino acid substitutions, and a CDR3 of amino acid sequence SEQ ID NO: 6 with zero to two amino acid substitutions. In a preferred embodiment, an antibody of the invention may comprise a light chain variable region comprising a CDR1 of amino acid sequence SEQ ID NO: 1 with zero to two amino acid substitutions, a CDR2 of amino acid sequence SEQ ID NO: 2 with zero to two amino acid substitutions, a CDR3 of amino acid sequence SEQ ID NO:3, a heavy chain variable region comprising a CDR1 of amino acid sequence SEQ ID NO: 4 with zero to two amino acid substitutions, a CDR2 of amino acid sequence SEQ ID NO: 5 with zero to two amino acid substitutions, and a CDR3 of amino acid sequence SEQ ID NO: 6 with zero to two amino acid substitutions. In an exemplary embodiment, an antibody of the invention may comprise a light chain variable region comprising a CDR1 of amino acid sequence SEQ ID NO: 1, a CDR2 of amino acid sequence SEQ ID NO: 2, a CDR3 of amino acid sequence SEQ ID NO:3, a heavy chain variable region comprising a CDR1 of amino acid sequence SEQ ID NO: 4, a CDR2 of amino acid sequence SEQ ID NO: 5, and a CDR3 of amino acid sequence SEQ ID NO: 6. The invention also encompasses the corresponding nucleic acid sequences of SEQ ID NO:1, 2, 3, 4, 5, and 6, which can readily be determined by one of skill in the art, and may be incorporated into a vector or other large DNA molecule, such as a chromosome, in order to express an antibody of the invention.

In another embodiment, an antibody of the invention may comprise a light chain variable region comprising a CDR1 of amino acid sequence SEQ ID NO: 7 with zero to two amino acid substitutions, a CDR2 of amino acid sequence SEQ ID NO: 8 with zero to two amino acid substitutions, and a CDR3 of amino acid sequence SEQ ID NO: 9 with zero to two amino acid substitutions, or may comprise a heavy chain variable region comprising a CDR1 of amino acid sequence SEQ ID NO: 10 with zero to two amino acid substitutions, a CDR2 of amino acid sequence SEQ ID NO: 11 with zero to two amino acid substitutions, and a CDR3 of amino acid sequence SEQ ID NO: 12 with zero to two amino acid substitutions. In a preferred embodiment, an antibody of the invention may comprise a light chain variable region comprising a CDR1 of amino acid sequence SEQ ID NO: 7 with zero to two amino acid substitutions, a CDR2 of amino acid sequence SEQ ID NO: 8 with zero to two amino acid substitutions, a CDR3 of amino acid sequence SEQ ID NO: 9 with zero to two amino acid substitutions, and a heavy chain variable region comprising a CDR1 of amino acid sequence SEQ ID NO: 10 with zero to two amino acid substitutions, a CDR2 of amino acid sequence SEQ ID NO: 11 with zero to two amino acid substitutions, and a CDR3 of amino acid sequence SEQ ID NO: 12 with zero to two amino acid substitutions. In an exemplary embodiment, an antibody of the invention may comprise a light chain variable region comprising a CDR1 of amino acid sequence SEQ ID NO: 7, a CDR2 of amino acid sequence SEQ ID NO: 8, a CDR3 of amino acid sequence SEQ ID NO: 9, a heavy chain variable region comprising a CDR1 of amino acid sequence SEQ ID NO: 10, a CDR2 of amino acid sequence SEQ ID NO: 11, and a CDR3 of amino acid sequence SEQ ID NO: 12. The invention also encompasses the corresponding nucleic acid sequences of SEQ ID NO: 7, 8, 9, 10, 11, and 12, which can readily be determined by one of skill in the art, and may be incorporated into a vector or other large DNA molecule, such as a chromosome, in order to express an antibody of the invention.

In one embodiment, an antibody of the invention may comprise a light chain variable region comprising a CDR1 of amino acid sequence SEQ ID NO: 21 (QXSQphXR, wherein X is any amino acid, p is a polar amino acid and h is a hydrophobic amino acid), a CDR2 of amino acid sequence SEQ ID NO: 22 (XhXpLXS, wherein X is any amino acid, p is a polar amino acid and h is a hydrophobic amino acid), and/or a CDR3 of amino acid sequence Leu-Gly-h (wherein h is a hydrophobic residue), or may comprise a heavy chain variable region comprising a CDR1 of amino acid sequence Tyr-X-Ile (wherein X is any amino acid), a CDR2 of amino acid sequence SEQ ID NO: 23 (AXYAXWXKG, wherein X is any amino acid), and/or a CDR3 of amino acid sequence SEQ ID NO: 24 (hXXGGhhXX, wherein X is any amino acid and h is a hydrophobic amino acid). In another embodiment, an antibody of the invention may comprise a light chain variable region comprising a CDR1 of amino acid sequence SEQ ID NO: 21 (QXSQphXR, wherein X is any amino acid, p is a polar amino acid and h is a hydrophobic amino acid), a CDR2 of amino acid sequence SEQ ID NO: 22 (XhXpLXS, wherein X is any amino acid, p is a polar amino acid and h is a hydrophobic amino acid), and a CDR3 of amino acid sequence Leu-Gly-h (wherein h is a hydrophobic residue), and may comprise a heavy chain variable region comprising a CDR1 of amino acid sequence Tyr-X-Ile (wherein X is any amino acid), a CDR2 of amino acid sequence SEQ ID NO: 23 (AXYAXWXKG, wherein X is any amino acid), and a CDR3 of amino acid sequence SEQ ID NO: 24 (hXXGGhhXX, wherein X is any amino acid and h is a hydrophobic amino acid). In still another embodiment, an antibody of the invention may comprise a light chain variable region comprising a CDR3 of amino acid sequence Leu-Gly-h (wherein h is a hydrophobic residue), and/or may comprise a heavy chain variable region comprising a CDR3 of amino acid sequence SEQ ID NO: 24 (hXXGGhhXX, wherein X is any amino acid and h is a hydrophobic amino acid). In each of the foregoing embodiments, SEQ ID NO: 21 may further comprise 1, 2, 3 or 4 amino acids on the C-terminus; Leu-Gly-h may further comprise 1, 2, 3, 4, 5, 6, 7, 8, 9 or 10 amino acids on the C-terminus; Tyr-X-Ile may further comprise 1 amino acid on the C-terminus and/or 1 amino acid on the N-terminus; SEQ ID NO: 23 may further comprise 1, 2, 3, 4, 5, 6 or 7 amino acids on the N-terminus; SEQ ID NO: 24 may further comprise 1 amino acid on the C-terminus.

As used herein, a polar amino acid is selected from the group consisting of serine, threonine, asparagine, and glutamine and a hydrophobic amino acid is selected from the group consisting of alanine, valine, isoleucine, leucine, methionine, phenylalanine, tyrosine and tryptophan.

TABLE C

Sequence Listing

| SEQ ID NO: | Description | SEQUENCE |
|---|---|---|
| 1 | mAb 14-12 and 14-7 LC CDR1 | QASQSISRQVS |
| 2 | mAb 14-12 and 14-7 LC CDR2 | RASTLAS |
| 3 | mAb 14-12 and 14-7 LC CDR3 | LGIVTDRIADGLA |
| 4 | mAb 14-12 and 14-7 HC CDR1 | AYGIN |
| 5 | mAb 14-12 and 14-7 HC CDR2 | FSAPHTASYARWTKG |
| 6 | mAb 14-12 and 14-7 HC CDR3 | YDRGGMVFNL |
| 7 | mAb 22-8 LC CDR1 | QSSQNVFRKNYLS |
| 8 | mAb 22-8 LC CDR2 | YIDSLTS |
| 9 | mAb 22-8 LC CDR3 | LGVDGSANDAT |
| 10 | mAb 22-8 HC CDR1 | NYYII |
| 11 | mAb 22-8 HC CDR2 | ITYGGGFAYYASWAKG |
| 12 | mAb 22-8 HC CDR3 | AAAGGAYDL |
| 13 | mAb 14-12 and 14-7 LC AA sequence | MDTRAPTQLLGLLLLWLPGATFALVMTQTPSSVPAAVGGTVTIGCQA SQSISRQVSWYQQKPGQPPKLLIYRASTLASGVSSRFKGSGSGTEFT LTISGVQCDDAATYYCLGIVTDRIADGLAFGGGTEVVVKGDPVAPTVLI FPPAADQVATGTVTIVCVANKYFPDVTVTVVEVDGTTQTTGIENSKTP QNSADCTYNLSSTLTLTSTQYNSHKEYTCKVTQGTTSVVQSFNRGDC |
| 14 | mAb 14-12 and 14-7 HC AA sequence | METGLRWLLLVAVLKGVQCQSVEESGGRLVTPGTPLTLTCTVSGFSI NAYGINWVRQAPGKGLEYIGFSAPHTASYARWTKGRFTMSRTSTTV DLRMTSPTTEDTATYFCARYDRGGMVFNLWGQGTLVTVSSGQPKAP SVFPLAPCCGDTPSSTVTLGCLVKGYLPEPVTVTWNSGTLTNGVRTF PSVRQSSGLYSLSSVVSVTSSSQPVTCNVAHPATNTKVDKTVAPSTC SKPTCPPPELLGGPSVFIFPPKPKDTLMISRTPEVTCVVVDVSQDDPE VQFTWYINNEQVRTARPPLREQQFNSTIRVVSTLPIAHQDWLRGKEF KCKVHNKALPAPIEKTISKARGQPLEPKVYTMGPPREELSSRSVSLTC MINGFYPSDISVEWEKNGKAEDNYKTTPAVLDSDGSYFLYSKLSVPT SEWQRGDVFTCSVMHEALHNHYTQKSISRSPGK |
| 15 | mAb 22-8 LC AA sequence | MDTRAPTQLLGLLLLWLPGATFAIEMTQTPSPVSAVVGGTVTINCQSS QNVFRKNYLSWFQQKPGQPPKLLISYIDSLTSGVPSRFSGSGAGTQF TLTISDVQCDDAATYYCLGVDGSANDATFGGGTEVVVEGDPVAPTVL IFPPAADQVATGTVTIVCVANKYFPDVTVTWEVDGTTQTTGIENSKTP QNSADCTYNLSSTLTLTSTQYNSHKEYTCKVTQGTTSVVQSFNRGDC |
| 16 | mAb 22-8 HC variable domain | METGLRWLLLLVAVLKGVQCQSLEESGGRLVTPGGSLTLTCTASGLTI NNYYIIWVRQAPGKGLKYIGITYGGGFAYYASWAKGRFTISRTSTTVD LKMTSLTAEDTATYFCVRAAAGGAYDLWGQGTLVTVSSGQPKAPSV FPLAPCCGDTPSSTVTLGCLVKGYLPEPVTVTWNSGTLTNGVRTFPS VRQSSGLYSLSSVVSVTSSSQPVTCNVAHPATNTKVDKTVAPSTCSK PTCPPPELLGGPSVFIFPPKPKDTLMISRTPEVTCVVVDVSQDDPEVQ FTWYINNEQVRTARPPLREQQFNSTIRVVSTLPIAHQDWLRGKEFKC KVHNKALPAPIEKTISKARGQPLEPKVYTMGPPREELSSRSVSLTCMI NGFYPSDISVEWEKNGKAEDNYKTTPAVLDSDGSYFLYSKLSVPTSE WQRGDVFTCSVMHEALHNHYTQKSISRSPGK |

TABLE C-continued

Sequence Listing

| SEQ ID NO: | Description | SEQUENCE |
|---|---|---|
| 17 | mAb 14-12 and 14-7 LC NT sequence | ATGGACACGAGGGCCCCCACTCAGCTGCTGGGGCTCCTGCTGCT CTGGCTCCCAGGTGCCACATTTGCCCTGGTGATGACCCAGACTCC ATCCTCCGTGCCTGCCGCTGTGGGAGGCACAGTCACCATCGGTT GCCAGGCCAGTCAGAGTATTAGTAGGCAAGTATCCTGGTATCAGC AGAAACCAGGGCAGCCTCCCAAGCTCCTGATCTACAGGGCATCCA CTCTGGCATCTGGGGTCTCATCGCGGTTCAAAGGCAGTGGATCTG GGACAGAGTTCACTCTCACTATTAGCGGCGTCCAGTGTGACGATG CTGCCACTTACTACTGTCTAGGTATTGTTACTGACCGTATTGCTGA TGGGCTTGCTTTCGGCGGAGGGACCGAGGTGGTGGTCAAAGGTG ATCCAGTTGCACCTACTGTCCTCATCTTCCCACCAGCTGCTGATCA GGTGGCAACTGGAACAGTCACCATCGTGTGTGTGGCGAATAAATA CTTTCCCGATGTCACCGTCACCTGGGAGGTGGATGGCACCACCCA AACAACTGGCATCGAGAACAGTAAAACACCGCAGAATTCTGCAGA TTGTACCTACAACCTCAGCAGCACTCTGACACTGACCAGCACACA GTACAACAGCCACAAAGAGTACACCTGCAAGGTGACCCAGGGCA CGACCTCAGTCGTCCAGAGCTTCAATAGGGGTGACTGTTAG |
| 18 | mAb 14-12 and 14-7 HC NT sequence | ATGGAGACTGGGCTGCGCTGGCTTCTCCTGGTCGCTGTGCTCAAA GGTGTCCAGTGTCAGTCGGTGGAGGAGTCCGGGGGTCGCCTAGT CACGCCTGGGACACCCTGACACTCACCTGCACAGTCTCTGGATT CAGCATCAATGCCTATGGAATTAACTGGGTCCGCCAGGCTCCAGG GAAGGGGCTGGAATACATCGGATTCAGTGCTCCTCATACCGCATC CTACGCGAGGTGGACAAAGGGCCGATTCACCATGTCCAGAACCTC GACCACGGTGGATCTGAGAATGACCAGCCCAACAACCGAGGACA CGGCCACCTACTTTTGTGCCAGATATGATCGGGGTGGGATGGTAT TTAACTTGTGGGGCCAAGGCACCCTGGTCACCGTCTCCTCAGGGC AACCTAAGGCTCCATCAGTCTTCCCACTGGCCCCCTGCTGCGGGG ACACACCCAGCTCCACGGTGACCCTGGGCTGCCTGGTCAAAGGG TACCTCCCGGAGCCAGTGACCGTGACCTGGAACTCGGGCACCCT CACCAATGGGGTACGCACCTTCCCGTCCGTCCGGCAGTCCTCAG GCCTCTACTCGCTGAGCAGCGTGGTGAGCGTGACCTCAAGCAGC CAGCCCGTCACCTGCAACGTGGCCCACCCAGCCACCAACACCAA AGTGGACAAGACCGTTGCGCCCTCGACATGCAGCAAGCCCACGT GCCCACCCCCTGAACTCCTGGGGGACCGTCTGTCTTCATCTTCC CCCCAAAACCCAAGGACACCCTCATGATCTCACGCACCCCCGAGG TCACATGCGTGGTGGTGGACGTGAGCCAGGATGACCCCGAGGTG CAGTTCACATGGTACATAAACAACGAGCAGGTGCGCACCGCCCG GCCGCCGCTACGGGAGCAGCAGTTCAACAGCACGATCCGCGTGG TCAGCACCCTCCCCATCGCGCACCAGGACTGGCTGAGGGGCAAG GAGTTCAAGTGCAAAGTCCACAACAAGGCACTCCCGGCCCCCATC GAGAAAACCATCTCCAAAGCCAGAGGGCAGCCCCTGGAGCCGAA GGTCTACACCATGGGCCCTCCCCGGGAGGAGCTGAGCAGCAGGT CGGTCAGCCTGACCTGCATGATCAACGGCTTCTACCCTTCCGACA TCTCGGTGGAGTGGGAGAAGAACGGGAAGGCAGAGGACAACTAC AAGACCACGCCGGCCGTGCTGGACAGCGACGGCTCCTACTTCCT CTACAGCAAGCTCTCAGTGCCCACGAGTGAGTGGCAGCGGGGCG ACGTCTTCACCTGCTCCGTGATGCACGAGGCCTTGCACAACCACT ACACGCAGAAGTCCATCTCCCGCTCTCCGGGTAAATGA |
| 19 | mAb 22-8 LC NT sequence | ATGGACACGAGGGCCCCCACTCAGCTGCTGGGGCTCCTGCTGCT CTGGCTCCCAGGTGCCACATTTGCCCATTGAAATGACCCAGACTCC ATCCCCTGTGTCTGCAGTTGTGGGAGGCACAGTCACCATCAATTG TCAGTCCAGTCAGAACGTTTTTCGTAAGAACTATTTATCCTGGTTT CAGCAGAAACCAGGGCAGCCTCCCAAGCTCCTGATCAGTTATATA GACAGTCTGACATCTGGGGTCCCATCGCGATTCAGCGGCAGTGG AGCTGGGACACAGTTCACTCTCACCATCAGTGACGTGCAGTGTGA CGATGCTGCCACTTATTACTGTTTAGGCGTTGATGGTAGTGCTAAT GATGCTACTTTCGGCGGAGGGACCGAGGTGGTGGTCGAAGGTGA TCCAGTTGCACCTACTGTCCTCATCTTCCCACCAGCTGCTGATCAG GTGGCAACTGGAACAGTCACCATCGTGTGTGTGGCGAATAAATAC TTTCCCGATGTCACCGTCACCTGGGAGGTGGATGGCACCACCCAA ACAACTGGCATCGAGAACAGTAAAACACCGCAGAATTCTGCAGAT TGTACCTACAACCTCAGCAGCACTCTGACACTGACCAGCACACAG TACAACAGCCACAAAGAGTACACCTGCAAGGTGACCCAGGGCAC GACCTCAGTCGTCCAGAGCTTCAATAGGGGTGACTGTTAG |
| 20 | mAb 22-8 HC NT sequence | ATGGAGACTGGGCTGCGCTGGCTTCTCCTGGTCGCTGTGCTCAAA GGTGTCCAGTGTCAGTCGCTGGAGGAGTCCGGGGGTCGCCTGGT AACGCCTGGAGGATCCCTGACACTCACCTGCACAGCCTCTGGACT CACCATCAATAACTACTACATAATTTGGGTCCGCCAGGCTCCAGG AAAGGGGCTGAAATACATCGGAATCACCTATGGTGGTGGTTTTGC ATACTACGCGAGCTGGGCGAAAGGCCGATTCACCATCTCCAGAAC CTCGACCACGGTGGATCTGAAAATGACCAGTCTGACAGCCGAGGA |

TABLE C-continued

Sequence Listing

| SEQ ID NO: | Description | SEQUENCE |
|---|---|---|
|  |  | CACGGCCACTTATTTCTGTGTCAGAGCTGCGGCTGGTGGTGCTTA<br>TGATTTGTGGGGCCAAGGCACCCTGGTCACCGTCTCCTCAGGGC<br>AACCTAAGGCTCCATCAGTCTTCCCACTGGCCCCCTGCTGCGGGG<br>ACACACCCAGCTCCACGGTGACCCTGGGCTGCCTGGTCAAAGGG<br>TACCTCCCGGAGCCAGTGACCGTGACCTGGAACTCGGGCACCCT<br>CACCAATGGGGTACGCACCTTCCCGTCCGTCCGGCAGTCCTCAG<br>GCCTCTACTCGCTGAGCAGCGTGGTGAGCGTGACCTCAAGCAGC<br>CAGCCCGTCACCTGCAACGTGGCCCACCCAGCCACCAACACCAA<br>AGTGGACAAGACCGTTGCGCCCTCGACATGCAGCAAGCCCACGT<br>GCCCACCCCCTGAACTCCTGGGGGGACCGTCTGTCTTCATCTTCC<br>CCCCAAAACCCAAGGACACCCTCATGATCTCACGCACCCCCGAGG<br>TCACATGCGTGGTGGTGGACGTGAGCCAGGATGACCCCGAGGTG<br>CAGTTCACATGGTACATAAACAACGAGCAGGTGCGCACCGCCCG<br>GCCGCCGCTACGGGAGCAGCAGTTCAACAGCACGATCCGCGTGG<br>TCAGCACCCTCCCCATCGCGCACCAGGACTGGCTGAGGGGCAAG<br>GAGTTCAAGTGCAAAGTCCACAACAAGGCACTCCCGGCCCCCATC<br>GAGAAAACCATCTCCAAAGCCAGAGGGCAGCCCCTGGAGCCGAA<br>GGTCTACACCATGGGCCCTCCCCGGGAGGAGCTGAGCAGCAGGT<br>CGGTCAGCCTGACCTGCATGATCAACGGCTTCTACCCTTCCGACA<br>TCTCGGTGGAGTGGGAGAAGAACGGGAAGGCAGAGGACAACTAC<br>AAGACCACGCCGGCCGTGCTGGACAGCGACGGCTCCTACTTCCT<br>CTACAGCAAGCTCTCAGTGCCCACGAGTGAGTGGCAGCGGGGCG<br>ACGTCTTCACCTGCTCCGTGATGCACGAGGCCTTGCACAACCACT<br>ACACGCAGAAGTCCATCTCCCGCTCTCCGGGTAAATGA |
| 21 | LC CDR1 | QXSQphXR, wherein X is any amino acid, p is a polar amino acid and h is a hydrophobic amino acid |
| 22 | LC CDR2 | XhXpLXS; wherein X is any amino acid, p is a polar amino acid and h is a hydrophobic amino acid |
|  | LC CDR3 | LGh; wherein h is a hydrophobic amino acid |
|  | HC CDR1 | YXI, wherein X is any amino acid |
| 23 | HC CDR2 | AXYAXWXKG, wherein X is any amino acid |
| 24 | HC CDR3 | hXXGGhhXX, wherein X is any amino acid and h is a hydrophobic amino acid |

II. Methods of Using Anti-Acetaminophen-Protein Adduct Antibodies

In an aspect, the present disclosure provides antibodies to detect acetaminophen-protein adducts in a biological sample obtained from a subject. In another aspect, the present disclosure provides antibodies to measure the amount of acetaminophen-protein adducts in a biological sample obtained from a subject. The amount of acetaminophen-protein adducts in a biological sample obtained from a subject can be used to classify a subject as having high or low amounts of acetaminophen-protein adducts, and may be further used to identify in the subject exposure and/or toxicity associated with acetaminophen. In a specific embodiment, the acetaminophen-protein adduct is 3-(cystein-S-yl)acetaminophen-protein adduct.

(a) Methods to Detect and Measure the Amount of Acetaminophen-Protein Adduct in a Biological Sample In an aspect, the disclosure provides means to detect acetaminophen-protein adduct in a biological sample obtained from a subject. In another aspect, the disclosure provides means to measure the amount of acetaminophen-protein adduct in a biological sample obtained from a subject. The method generally comprises detecting and/or measuring the amount of one or more acetaminophen-protein adduct in a biological sample obtained from a subject using an antibody that specifically binds acetaminophen-protein adduct. Additionally, the method may comprise (i) obtaining a biological sample from a subject, and (ii) detecting and/or measuring the amount of one or more acetaminophen-protein adduct in the sample using an antibody that specifically binds acetaminophen-protein adduct. Suitable antibodies are described above in Section I.

As used herein, the term "subject" refers to a living organism that may be administered acetaminophen. Suitable subjects include, but are not limited to, a human, a livestock animal, a companion animal, a lab animal, and a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In specific embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In a preferred embodiment, the subject is human. Subjects may be of any age, including newborn, adolescent, adult, middle age, or elderly.

A subject may or may not be having a symptom associated with acetaminophen-induced toxicity. Specifically, the acetaminophen-induced toxicity may be hepatotoxicity. A skilled artisan will appreciate that pathological acetaminophen-induced toxicity likely commences prior to diagnosis or the onset of symptoms associated with acetaminophen-induced toxicity. In some embodiments, a subject is having a symptom associated with acetaminophen-induced toxicity. In other embodiments, a subject is not having a symptom associated with acetaminophen-induced toxicity. In still other embodiments, a subject has detectable acetaminophen-induced toxicity but is not having any other symptom associated with acetaminophen-induced toxicity. In yet still other embodiments, a subject has received acetaminophen. In different embodiments, a subject has received a supratherapeutic dose of acetaminophen. In alternative embodiments, a subject has been suspected of receiving a supratherapeutic dose of acetaminophen. For example, a subject may have liver failure of unclear etiology which may have developed as a result of receiving a supratherapeutic dose of acetaminophen. Early diagnosis of acetaminophen-induced toxicity in the subject may reduce the development and/or progression of symptoms associated with the pathological acetaminophen-induced toxicity.

Exemplary symptoms associated with acetaminophen-induced hepatotoxicity may include, but are not limited to, anorexia, nausea, vomiting, right upper quadrant abdominal pain, elevated AST, ALT, bilirubin and PT (INR), renal failure, pancreatitis, multiple organ failure. Mild acetaminophen poisoning may not cause symptoms, and when present, symptoms are usually minor until ≥48 h after ingestion. In some embodiments, the severity of symptoms of acetaminophen toxicity are quantified using 4 stages as shown in Table D.

TABLE D

Stages of acute acetaminophen poisoning

| Stage | Time Postingestion | Description |
| --- | --- | --- |
| I | 0-24 h | Anorexia, nausea, vomiting |
| II | 24-72 h | Right upper quadrant abdominal pain (common) |
| | | AST, ALT, and, if poisoning is severe, bilirubin and PT (INR) sometimes elevated |
| III | 72-96 h | Vomiting and symptoms of liver failure |
| | | Peaking of AST, ALT, bilirubin and INR |
| | | Sometimes renal failure and pancreatitis |
| IV | >5 days | Resolution of hepatotoxicity or progression to multiple organ failure (sometimes fatal) |

As used herein, the term "biological sample" refers to a sample obtained from a subject. Any biological sample comprising an acetaminophen-protein adduct is suitable. Numerous types of biological samples are known in the art. Suitable biological samples may include, but are not limited to, hair, tissue samples or bodily fluids. In some embodiments, the biological sample is a tissue sample such as a tissue biopsy. The tissue biopsy may be a biopsy of liver tissue. The biopsied tissue may be fixed, embedded in paraffin or plastic, and sectioned, or the biopsied tissue may be frozen and cryosectioned. Alternatively, the biopsied tissue may be processed into individual cells or an explant, or processed into a homogenate, a cell extract, a membranous fraction, or a protein extract. In other embodiments, the sample may be a bodily fluid. Non-limiting examples of suitable bodily fluids include blood, plasma, serum, urine, saliva, semen, perspiration, tears, mucus, sputum, tissue lystates or other excrement (e.g. feces). In a specific embodiment, the bodily fluid is urine. In another specific embodiment, the bodily fluid is plasma. In still another specific embodiment, the bodily fluid is serum. In yet still another specific embodiment, the bodily fluid is saliva. The fluid may be used "as is", the cellular components may be isolated from the fluid, or a protein fraction may be isolated from the fluid using standard techniques. In a different embodiment, the biological sample is hair.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that an acetaminophen-protein adduct can be accurately detected and the amount measured according to the invention.

In some embodiments, a single sample is obtained from a subject to detect an acetaminophen-protein adduct in the sample. Alternatively, an acetaminophen-protein adduct may be detected in samples obtained over time from a subject. As such, more than one sample may be collected from a subject over time. For instance, 2, 3, 4, 5, 6, 7, 8, 9, 10, 11, 12, 13, 14, 15, 16 or more samples may be collected from a subject over time. In some embodiments, 2, 3, 4, 5, or 6 samples are collected from a subject over time. In other embodiments, 6, 7, 8, 9, or 10 samples are collected from a subject over time. In yet other embodiments, 10, 11, 12, 13, or 14 samples are collected from a subject over time. In other embodiments, 14, 15, 16 or more samples are collected from a subject over time.

When more than one sample is collected from a subject over time, samples may be collected every 0.5, 1, 2, 3, 4, 5, 6, 7, 8, 9, 10, 11, 12 or more hours. In some embodiments, samples are collected every 0.5, 1, 2, 3, or 4 hours. In other embodiments, samples are collected every 4, 5, 6, or 7 hours. In yet other embodiments, samples are collected every 7, 8, 9, or 10 hours. In other embodiments, samples are collected every 10, 11, 12 or more hours. Additionally, samples may be collected every 1, 2, 3, 4, 5, 6, 7, 8, 9, 10, 11, 12 or more days. In some embodiments, a sample is collected about every 6 days. In some embodiments, samples are collected every 1, 2, 3, 4, or 5 days. In other embodiments, samples are collected every 5, 6, 7, 8, or 9 days. In yet other embodiments, samples are collected every 9, 10, 11, 12 or more days.

Once a sample is obtained, it is processed in vitro in order to detect and measure the amount of one or more acetaminophen-protein adduct using an anti-acetaminophen-protein adduct antibody. All suitable methods for detecting and measuring an amount of protein using an antibody known to one of skill in the art are contemplated within the scope of the invention. Methods for detecting and measuring an amount of protein using an antibody (i.e. "antibody-based methods") are well known in the art. Non-limiting examples include an ELISA, a lateral flow assay, a sandwich immunoassay, a radioimmunoassay, an immunoblot or Western blot, flow cytometry, immunohistochemistry, and an array. A lateral flow assay may be a device intended to detect the presence (or absence) of a target analyte in sample.

In general, an antibody-based method of detecting and measuring an amount of an acetaminophen-protein adduct comprises contacting some or all of the sample comprising an acetaminophen-protein adduct with an anti-acetaminophen-protein adduct antibody under conditions effective to allow for formation of a complex between the antibody and the acetaminophen-protein adduct. Typically, the entire sample is not needed, allowing one skilled in the art to repeatedly detect and measure the amount of an acetaminophen-protein adduct in the sample over time. The method may occur in solution, or the antibody or acetaminophen-protein adduct may be immobilized on a solid surface. Non-limiting examples of suitable surfaces include microtitre plates, test tubes, beads, resins, and other polymers. Attachment to the substrate may occur in a wide variety of ways, as will be appreciated by those in the art. For example, the substrate and the antibody may be derivatized with chemical functional groups for subsequent attachment of the two. For example, the substrate may be derivatized with a chemical functional group including, but not limited to, amino groups, carboxyl groups, oxo groups or thiol groups. Using these functional groups, the antibody may be attached directly using the functional groups or indirectly using linkers. An anti-acetaminophen-protein adduct antibody may also be attached to the substrate non-covalently. For example, a biotinylated anti-acetaminophen-protein adduct antibody may be prepared, which may bind to surfaces covalently coated with streptavidin, resulting in attachment. Alternatively, an antibody may be synthesized on the surface using techniques such as photopolymerization and photolithography.

Contacting the sample with an antibody under effective conditions for a period of time sufficient to allow formation of a complex generally involves adding the anti-acetaminophen-protein adduct antibody composition to the sample and incubating the mixture for a period of time long enough for the anti-acetaminophen-protein adduct antibody to bind to any antigen present. After this time, the complex may be washed and then the complex is detected and the amount measured by any method well known in the art. Methods of detecting and measuring an amount of an antibody-polypeptide complex are generally based on the detection of a label or marker. The term "label", as used herein, refers to any substance attached to an antibody, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, $Ni^{2+}$, Flag tags, myc tags, heavy metals, and enzymes (including alkaline phosphatase, peroxidase, glucose oxidase and luciferase). Methods of detecting and measuring an amount of an antibody-polypeptide complex based on the detection of a label or marker are well known in the art.

In some embodiments, an antibody-based method is an immunoassay. Immunoassays can be run in a number of different formats. Generally speaking, immunoassays can be divided into two categories: competitive immmunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled). Suitable labels are described above.

In other embodiments, an antibody-based method is an immunoblot or Western blot. In yet other embodiments, an antibody-based method is flow cytometry. In different embodiments, an antibody-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

In alternative embodiments, an antibody-based method is an array. An array comprises at least one address, wherein at least one address of the array has disposed thereon an anti-acetaminophen-protein adduct antibody. Arrays may comprise from about 1 to about several hundred thousand addresses. Several substrates suitable for the construction of arrays are known in the art, and one skilled in the art will appreciate that other substrates may become available as the art progresses. Suitable substrates are also described above. In some embodiments, the array comprises at least one anti-acetaminophen-protein adduct antibody attached to the substrate is located at one or more spatially defined addresses of the array. For example, an array may comprise at least one, at least two, at least three, at least four, or at least five anti-acetaminophen-protein adduct antibodies, each antibody recognizing the same or different acetaminophen-protein adducts, and each antibody may be may be at one, two, three, four, five, six, seven, eight, nine, ten or more spatially defined addresses.

For each of the foregoing embodiments, an acetaminophen-protein adduct may be first isolated or enriched before detection. For instance, an acetaminophen-protein adduct may be enriched or isolated using liquid chromatography, by precipitation, electrophoresis, or affinity purification. In some embodiments, an acetaminophen-protein adduct may be enriched or purified using liquid chromatography. In other embodiments, an acetaminophen-protein adduct may be enriched or purified using electrophoresis.

In an embodiment, an acetaminophen-protein adduct may be enriched or purified by affinity purification before detection. In another embodiment, an acetaminophen-protein adduct may be enriched or purified by affinity purification using an antibody of the invention. Methods of enriching a sample for a protein or purifying a protein using affinity purification are known in the art. In short, affinity purification comprises incubating a sample with a solid support, such as beads, a culture plate, or a membrane, that facilitates later steps. A solid support may be coated with an antibody of the invention, causing an acetaminophen-protein adduct to attach to the solid support. Alternatively, a sample may be incubated with an antibody of the invention, and the acetaminophen-protein adduct-antibody complex may be isolated by incubating with a solid support coated with a second antibody with specificity to an antibody of the invention, causing a protein-antibody complex to attach to the solid support. An acetaminophen-protein adduct may then be purified or enriched by washing other material in the sample that is not bound to the solid support, or, if the solid support is superparamagnetic beads, an acetaminophen-protein adduct attached to the beads (expressing the antigen) may be separated from the sample by attraction to a strong magnetic field. Upon enrichment or purification, an acetaminophen-protein adduct may then be detected in the enriched or purified sample using any of the methods described above.

In another embodiment, protein-specific antibodies may be used to capture and isolate adducted protein(s), and then an acetaminophen-protein adduct antibody of the disclosure may be used to detect the adduction of the protein. Suitable protein-specific antibodies may be antibodies that specifically bind a protein known to be modified with NAPQI. Non-limiting examples of proteins modified by NAPQI include betaine-homocysteine S-methyltransferase 1 (BHMT), cytoplasmic aspartate aminotransferase (cAspAT), 1,4-alpha-glucan-branching enzyme, formimidoyltransferase-cyclodeaminase (FTCD), dystrophin, aldehyde dehydrogenase, ATP synthase alpha-chain mitochondrial, calregulin, carbamoylphosphate synthetase I, carbonate dehydratase III (CA-III), aldehyde dehydrogenase (AHD-M1), glutamate dehydrogenase (GDH), glutamate-ammonia ligase, cellular glutathione peroxidase, glutathione transferases (GST), glutathione S-transferase P 1, GAPDH, AdoMet synthetase 1, macrophage 23 kDa stress protein, eIF-4A-I, 56 kDa acetaminophen-binding protein, L-iditol 2-dehydrogenase, amine N-methyltransferase, antioxidant protein 1, tropomyosin 3, urate oxidase, 10-formyltetrahydrofolate dehydrogenase, hemoglobin, 56 kDa selenium-binding protein, lamin A, cellular thyroid hormone binding protein, 58 kDa microsomal protein, Life Tech mouse embryo 8 5dpc 10664019 *Mus musculus* cDNA clone, inorganic pyrophosphatase, NML *Mus musculus* cDNA clone, 2-4-dienoyl-CoA reductase mitochondrial, 3-HAI,3-hydroxyanthranilate 3-4-dioxygenase, 94 kDa glucose-regulated protein, cytosolic inhibitor of Nrf2, serum albumin, and delayed early response protein 6. One or more adducted proteins may be isolated and then an acetaminophen-protein adduct antibody of the disclosure may be used to detect the amount of adducted protein as described above.

(b) Methods to Detect Acetaminophen-Induced Toxicity in a Subject

In aspect, the disclosure provides means to classify a subject based on the amount of acetaminophen-protein adduct measured in a biological sample obtained from the subject. The method generally comprises (i) measuring the amount of acetaminophen-protein adduct in a biological sample obtained from the subject using an antibody that specifically binds acetaminophen-protein adduct, (ii) comparing the amount of acetaminophen-protein adduct in the sample to a reference value, and (iii) classifying the subject as having a high or low amount of acetaminophen-protein adduct based on the amount of acetaminophen-protein adduct measured in the sample. Optionally, the method may comprise (i) obtaining a biological sample from a subject and measuring the amount of acetaminophen-protein adduct in the sample using an antibody that specifically binds acetaminophen-protein adduct, (ii) comparing the amount of acetaminophen-protein adduct in the sample to a reference value, and (iii) classifying the subject as having a high or low amount of acetaminophen-protein adduct based on the amount of acetaminophen-protein adduct measured in the sample. In the foregoing methodologies, one or more acetaminophen protein adducts may be measured. For example, 1, 2, 3, 4, 5, 6, 7, 8, 9 or 10 acetaminophen protein adducts may be measured. Methods for obtaining a biological sample from a subject and measuring the amount of acetaminophen-protein adduct in the sample using an antibody that specifically binds acetaminophen-protein adduct are detailed above. In a preferred embodiment, the biological sample is biological fluid selected from the group consisting of blood, plasma, serum, urine and saliva. In a specific embodiment, the acetaminophen-protein adduct is 3-(cystein-S-yl)acetaminophen-protein adduct.

Any suitable reference value known in the art may be used. For example, a suitable reference value may be the amount of acetaminophen-protein adduct in a biological fluid sample obtained from a subject or group of subjects of the same species that has normal hepatic function. In another example, a suitable reference value may be the amount of acetaminophen-protein adduct in a biological fluid sample obtained from a subject, or group of subjects, of the same species that has no detectable acetaminophen-induced toxicity. In another example, a suitable reference value may be the amount of acetaminophen-protein adduct in biological fluid sample obtained from a subject or group of subjects of the same species that has acetaminophen-induced toxicity as measured by AST, ALT, bilirubin, INR or other non-specific biomarkers of hepatic function. For example, a suitable reference value may be the amount of acetaminophen-protein adduct in a biological sample obtained from a subject or group of subjects of the same species that has acetaminophen-induced toxicity as measured by ALT levels >1000 IU. In another example, a suitable reference value may be the background signal of the assay as determined by methods known in the art. In another example, a suitable reference value may be a measurement of the amount of acetaminophen-protein adduct in a reference sample obtained from the same subject. The reference sample comprises the same type of biological fluid as the test sample, and may or may not be obtained from the subject when hepatic function was normal. A skilled artisan will appreciate that it is not always possible or desirable to obtain a reference sample from a subject when the subject is otherwise healthy. For example, in an acute setting, a reference sample may be the first sample obtained from the subject at presentation. In another example, when monitoring the effectiveness of a therapy, a reference sample may be a sample obtained from a subject before therapy began. In such an example, a subject may have suspected acetaminophen-induced toxicity but may not have other symptoms of acetaminophen-induced toxicity or the subject may have suspected acetaminophen-induced toxicity and one or more other symptom of acetaminophen-induced toxicity. In a specific embodiment, a suitable reference value may be a threshold previously determined via other methods. For example, a suitable reference value may be a value corresponding to 1 nmol/ml of acetaminophen-protein adduct as measured by high pressure liquid chromatography with electrochemical detection (HPLC-EC).

According to the disclosure, a subject may be classified based on the amount of acetaminophen-protein adduct measured in the sample. Classifying a subject based on the amount of acetaminophen-protein adduct measured in a sample of biological fluid obtained from the subject may be used to identify subjects with acetaminophen-induced exposure and/or toxicity. The term "acetaminophen-induced toxicity" is described in detail below. Generally speaking, a subject may be classified as having a high or low amount of acetaminophen-protein adduct compared to a reference value, wherein a high amount of acetaminophen-protein adduct is an amount above the reference value and a low amount is an amount equal to or below the reference value. In preferred embodiments, to classify a subject as having a high amount of acetaminophen-protein adduct, the amount of acetaminophen-protein adduct in the sample compared to the reference value may be at least 5% greater. For example, the amount of acetaminophen-protein adduct in the sample may be at least 5%, at least 10%, at least 20%, at least 30%, at least 40%, at least 50%, at least 60%, at least 70%, at least 80%, at least 90%, or at least 100% greater than the reference value. In other embodiments, the amount of acetaminophen-protein adduct in the sample of biological fluid obtained from the subject compared to the reference value may be increased at least 2-fold. For example, the amount of acetaminophen-protein adduct in the sample compared to the reference value may be increased at least 2-fold, at least 5-fold, at least 10-fold, at least 15-fold, at least 20-fold, at least 25-fold, at least 30-fold, at least 35-fold, at least 40-fold, at least 45-fold, or at least 50-fold.

In another aspect, the disclosure provides means to detect acetaminophen-induced exposure and/or toxicity in a subject. As used herein, the term "acetaminophen-induced toxicity" refers to damage or destruction to the liver due to acetaminophen. Acetaminophen, when taken in overdoses and sometimes even when introduced within therapeutic ranges, may injure the liver. Damage to the liver is not due to the drug itself but to a toxic metabolite (N-acetyl-p-benzoquinone imine NAPQI, or NABQI) produced by cytochrome P-450 enzymes in the liver. In an overdose, a large amount of NAPQI is generated, which overwhelms the detoxification process and leads to liver cell damage. The risk of liver injury is influenced by several factors including the dose ingested, concurrent alcohol or other drug intake, interval between ingestion and antidote, etc. The dose toxic to the liver is quite variable from person to person and is smaller in chronic alcoholics.

The causes of hepatotoxicity known in the art are numerous, and may include, but are not limited to, trauma, neoplastic disease, bacterial or viral infection, exposure to toxins, poisons, environmental, or other substances. Biomarkers of liver function are well known in the art. Non-limiting examples of biomarkers of liver injury include elevated AST, ALT, bilirubin and PT (INR). However, increased acetaminophen-protein adduct in a biological fluid may prove that acetaminophen caused or contributed to the liver injury.

In addition to the detection of acetaminophen-induced toxicity, it should also be appreciated by those of skill in the art that a method of the disclosure may be used to diagnose various features of treatment with acetaminophen and acetaminophen toxicity. A method of the disclosure may be used to determine levels of acetaminophen intake by a subject to determine compliance with treatment. Alternatively, a method of the disclosure may be used to determine the severity of acetaminophen toxicity. For instance, a method of the disclosure may be used to determine normal sub-toxic levels of acetaminophen, thereby ruling out acetaminophen toxicity. A method of the disclosure may also be used to diagnose acetaminophen toxicity with good prognosis that will resolve. Alternatively, a method of the disclosure may be used to diagnose acetaminophen toxicity with bad prognosis that will lead to death or the need for a liver transplant. A method of the disclosure may also be used to determine chronic acetaminophen exposure. As used herein, the term "chronic acetaminophen exposure" may be used to describe acetaminophen toxicity caused by exposure to repeated supratherapeutic acetaminophen over extended periods of time, such as, for instance, through ingesting supratherapeutic doses of acetaminophen, or use of sustained release acetaminophen formulations. Additionally, a method of the disclosure may be used to determine acute acetaminophen exposure. As used herein, the term "acute acetaminophen exposure" may be used to describe acetaminophen toxicity caused by ingestion of a single large dose of acetaminophen.

A method of the present disclosure may be used in combination with other methods of diagnosing acetaminophen toxicity, or other clinical diagnostic methods. Additionally, a method of the present disclosure may further comprise treatment of a subject. Non-limiting examples of standard treatments for acetaminophen toxicity administration of activated charcoal, administration of N-acetylcysteine (oral or IV), liver transplantation, and combinations thereof.

For each aspect, the method generally comprises (i) measuring the amount of acetaminophen-protein adduct in a biological sample obtained from a subject using an antibody that specifically binds acetaminophen-protein adduct, and (ii) comparing the amount of acetaminophen-protein adduct in the sample to a reference value. Optionally, the method may comprise (i) obtaining a biological sample from a subject, (ii) measuring the amount of acetaminophen-protein adduct in the sample using an antibody that specifically binds acetaminophen-protein adduct, and (iii) comparing the amount of acetaminophen-protein adduct in the sample to a reference value. A greater amount of acetaminophen-protein adduct in the sample compared to the reference value indicates acetaminophen-induced toxicity. The amount of acetaminophen-protein adduct may be a qualitative, a semi-quantitative or quantitative measurement. Suitable anti-acetaminophen-protein adduct antibodies are described above, as are methods for measuring the amount of acetaminophen-protein adduct in a biological sample. In a preferred embodiment, the biological sample is biological fluid selected from the group consisting of blood, plasma, serum, urine and saliva.

III. Acetaminophen-Protein Adduct Immunogen

Another aspect of the present disclosure provides an acetaminophen-protein adduct immunogen for the production of antibodies with specificity for acetaminophen-protein adducts. The novel immunogen was prepared by modifying an immunogenic carrier protein (CP) with 2-iminothiolane (2-IT) to provide a highly substituted CP with numerous 5-carbon linker molecules with terminal sulfhydryl groups. This 2-IT modified CP was then covalently modified at the terminal sulfhydryl groups by reaction with biosynthetically prepared N-acetyl-p-benzoquinone imine (NAPQI). In a specific embodiment, the immunogen is Carrier Protein-2-iminothiolane linked-acetaminophen immunogen. Accordingly, the immunogen may be referred to as CP-2-IT-APAP.

As used herein, a "carrier protein" is any protein used for coupling with peptides or other haptens that are not sufficiently large or complex on their own to induce an immune response and produce antibodies. The carrier protein, because it is large and complex, confers immunogenicity to the conjugated hapten, resulting in antibodies being produced against epitopes on the hapten and carrier. Many proteins can be used as carriers and are chosen based on immunogenicity, solubility, and availability of useful functional groups through which conjugation with the hapten can be achieved. Non-limiting examples of suitable carrier proteins include keyhole limpet hemocyanin (KLH), bovine serum albumin (BSA), Blue Carrier Protein (Concholepas concholepas hemocyanin (CCH)) and ovalbumin (OVA).

2-iminothiolane may also be referred to as 2-IT or Traut's reagent. 2-iminothiolane is a small thiolation compound that reacts with primary amines to add a small spacer arm (8.1 angstroms) terminated by a free sulfhydryl group. 2-iminothiolane is a cyclic thioimidate compound for thiolation (sulfhydryl addition). 2-IT reacts with primary amines (—$NH_2$) to introduce sulfhydryl (—SH) groups while maintaining charge properties similar to the original amino group. Other linkers in place of 2-IT may be used in an immunogen of the invention provided the linker contains a sulfur bound at the carbon 3 position of the ring structure of acetaminophen. The presence of the sulfur is essential to forming an antibody of the invention. The linker may be 1, 2, 3, 4, 5, 6, 7, 8, 9, or 10 carbons. In a specific embodiment, the linker may be 3, 4, 5 or 6 carbons. In an exemplary embodiment, the linker is 5 carbons.

The carrier protein conjugated to a linker is reacted with NAPQI by methods common in the art. In a specific embodiment, the CP-2-IT is reacted with NAPQI by methods common in the art. It is essential that the sulfhydryl group of the linker attached to CP be reacted with NAPQI to obtain an immunogen of the invention. In a specific embodiment, the sulfhydryl group of the 2-IT may be targeted for reaction with NAPQI.

The inventors have discovered that immunization with CP-2-IT-APAP may produce monoclonal antibodies with specificity for acetaminophen-protein adducts. Specifically, immunization with CP-2-IT-APAP may produce monoclonal antibodies with specificity for 3-(cystein-S-yl)acetaminophen protein adduct. Methods of making a monoclonal antibody using an immunogen of the invention are described in Section I. Using an immunogen of the invention, a monoclonal antibody may bind to an acetaminophen protein adduct approximately 2000 to 3000 times more effectively than free acetaminophen. In another embodiment, a monoclonal antibody may bind to an acetaminophen protein adduct approximately 8000 times more effectively than free acetaminophen. For example, a monoclonal antibody may bind to an acetaminophen protein about 100, about 250, about 500, about 1000, about 1500, about 2000, about 2500, about 3000, about 3500, about 4000, about 4500, about 5000, about 5500, about 6000, about 6500, about 7000, about 7500, about 8000, about 8500, about 9000, about 9500, about 10,000, about 11,000, about 12,000, about 13,000, about 14,000, about 15,000, about 16,000, about 17,000, about 18,000, about 19,000 about 20,000, about 30,000, about 40,000, or about 50,000 times more effectively than free acetaminophen.

Definitions

As used herein, "antibody" refers to an immunoglobulin derived molecule that specifically recognizes acetaminophen-protein adduct. An antibody of the invention may be a full length antibody (IgM, IgG, IgA, IgE) or may be an antibody fragment (Fab, F(ab')2, scFv). An antibody may be chimeric or may be humanized.

As used herein, "CDR" means "complementary determining region." CDRs may also be referred to as hypervariable regions.

As used herein, "light chain" is the small polypeptide subunit of the antibody. A typical antibody comprises two light chains and two heavy chains.

As used herein, the "heavy chain" is the large polypeptide subunit of the antibody. The heavy chain of an antibody contains a series of immunoglobulin domains, with at least one variable domain and at least one constant domain.

"Humanized", as used herein, refers to the process where monoclonal antibodies are produced using recombinant DNA to create constructs capable of expression in human cell culture. Any known techniques for producing these constructs will work for purposes of the present invention.

As used herein, "single chain variable fragments" or "scFv" or "scFvs", refer to fusion proteins of the variable regions of the heavy and light chains of immunoglobulins connected via a linker. In some embodiment, the linker is a peptide of about 10 to 25 amino acids.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Production of Monoclonal Antibodies Specific for Acetaminophen-Protein Adduct The hepatotoxicity of acetaminophen (APAP) (also called paracetamol) is mediated by the reactive metabolite N-acetyl-p-benzoquinone imine which binds covalently to protein as 3-(cystein-S-yl)acetaminophen. These acetaminophen-protein adducts are specific biomarkers of exposure to acetaminophen and elevated levels of these adducts are a specific biomarker of acetaminophen toxicity. This disclosure is to describe a new and unique immunogen for the preparation of monoclonal antibodies with specificity for the acetaminophen-protein adduct. The resultant antibodies react specifically with the acetaminophen-protein adducts that are formed physiologically during the pathogenesis of acetaminophen-mediated toxicity.

The inventors conceived of and synthesized a new immunogen for the purpose of preparing antibodies with specificity for acetaminophen protein adducts. The new immunogen was prepared by modifying an immunogenic carrier protein (CP) with 2-iminothiolane (2-IT) to provide a highly substituted CP with numerous 5-carbon linker molecules with terminal sulfhydryl groups. This 2-IT modified CP was then covalently modified at the terminal sulfhydryl groups by reaction with synthetically prepared N-acetyl-p-benzoquinone imine. For shorthand reference, the Carrier Protein-2-iminothiolane linked-acetaminophen immunogen is referred to as CP-2-IT-APAP. Immunizing rabbits with CP-2-IT-APAP resulted in the production of polyclonal rabbit antibodies with specificity for the physiologically formed 3-(cystein-S-yl)acetaminophen protein adducts and this was confirmed by ELISA and Lateral Flow Immunoassay using acetaminophen proteins adducts as solid-phase antigen. Subsequently, the CP-2-IT-APAP immunogen was used to prepare rabbit monoclonal antibodies (mAb) with specificity for acetaminophen-protein adducts. To confirm binding of purified antibodies to acetaminophen-protein adducts, an ELISA was performed. In the ELISA experiment, antigen is coated overnight at 4° C. Samples are added in serial dilutions starting at 1:250 (supernatant and flow-through) or 4 µg/ml (purified antibody) and incubated at room temperature for 1.5 hours. Goat anti-rabbit alkaline phosphatase-conjugated secondary antibody is added at room temperature for 1 hour. Substrate solution is added and developed for 15 minutes at room temperature. Absorbance is measured at 405 nm. Data in FIG. 1 represents the average of repetitions (rep) 1 and 2 for each sample.

Example 2. Competitive ELISA to Determine the Relative Inhibitory Potency of APAP Bound to Protein as APAP-Protein Adduct Versus Free Unbound APAP Tissue culture supernatants from Rabbit monoclonal antibody clone 14-12 at a dilution of 1:250 was mixed with serial 4-fold dilutions of inhibitor (either BSA-APAP or APAP) such that the final dilution of RmAb was 1:500. The final concentrations of APAP were 80, 20, 5, 1.25, and 0.31 nmole per ELISA well. The final concentrations of APAP-BSA (quantified by HPLC-EC as APAP-Cys from the hydrolyzed protein) were 10, 2.5, 0.625, 0.156, and 0.04 pmole per ELISA well.

Selection of promising RmAb clones for future use to detect acetaminophen protein adducts was based on efficiency of immunoglobulin production, affinity for detection of APAP-protein adduct (3-(cystein-S-yl)acetaminophen), and relative insensitivity for detection of the free drug APAP.

Figure 2:
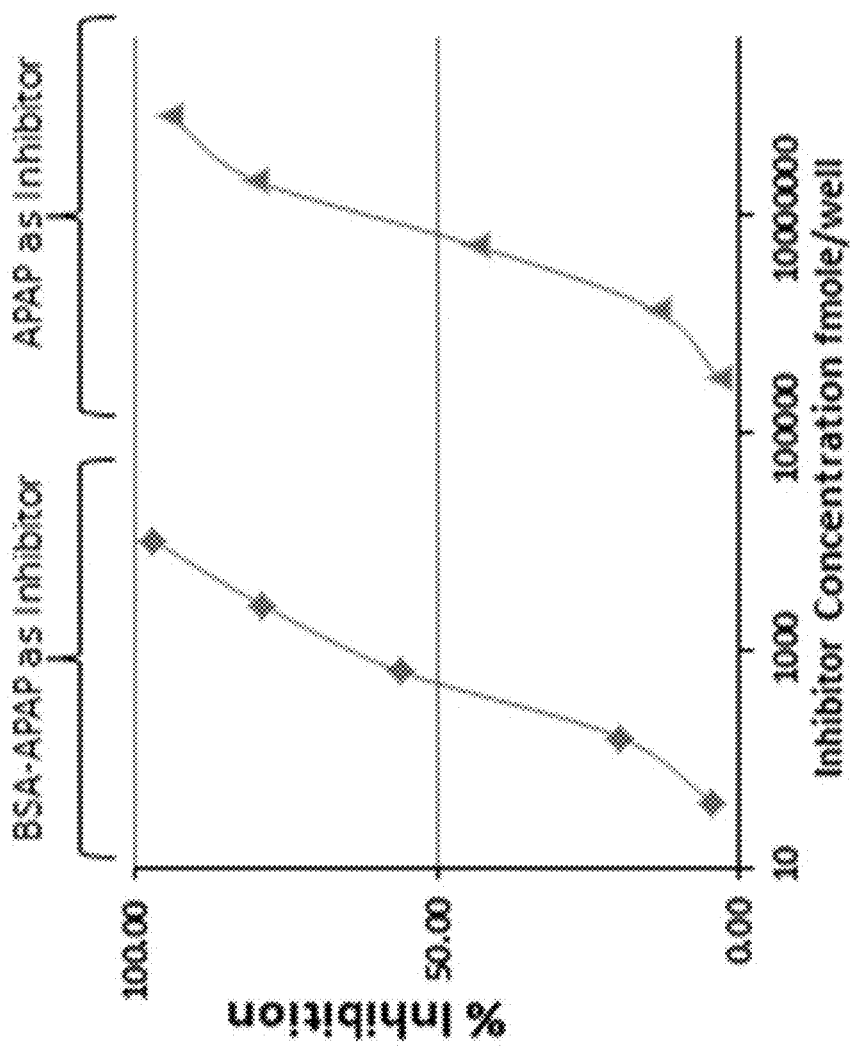
FIG. 2 depicts a competitive ELISA showing the specificity of antibody 14-12 for APAP-protein adducts versus free unbound APAP.

Synthetically prepared acetaminophen-protein adduct (BSA-APAP) and free drug (APAP) were evaluated in competitive ELISA to determine their relative capacity, on a molar basis, to inhibit the binding of clone 14-12 rabbit monoclonal antibody to solid-phase immobilized acetaminophen protein adduct. Data is plotted as percent inhibition and indicate that it takes approximately 8,000 free APAP molecules to produce the same inhibitory potency as one molecule of APAP-Cys as protein adduct (FIG. 2). Restated, clone 14-12 antibody has approximately 8000 times more affinity for acetaminophen protein adduct than it does for free APAP as measured in this ELISA context.

The competitive ELISA was repeated with rabbit monoclonal antibody (RMAb) 14-12 and rabbit monoclonal antibody (RMAb) 22-8. Briefly, ELISA plates were coated with BSA-APAP, 200 ng (protein)/well. RMAb clone subernatant (1:250 dilution) was combined with an equal volume of serial 4-fold dilutions of inhibitor to give a final antibody dilution of 1:500 and the indicated final concentrations of APAP-BSA and APAP. BSA-APAP prepared by reacting bovine serum albumin (BSA) with N-Acetyl-p-benzoquinone imine (NAPQI) to form 3-(cystein-S-yl) acetaminophen protein adducts on BSA (BSA-APAP). After incubation and washing, bound RMAb was detected using Goat anti-Rabbit-IgG conjugated to HRP followed by the substrate TMB and color development was determined using an ELISA plate reader. Dilution Buffer was 0.025% (w/v) non-fat milk protein in phosphate buffered saline containing 0.15 M NaCl, pH 7.4.

Figure 3:
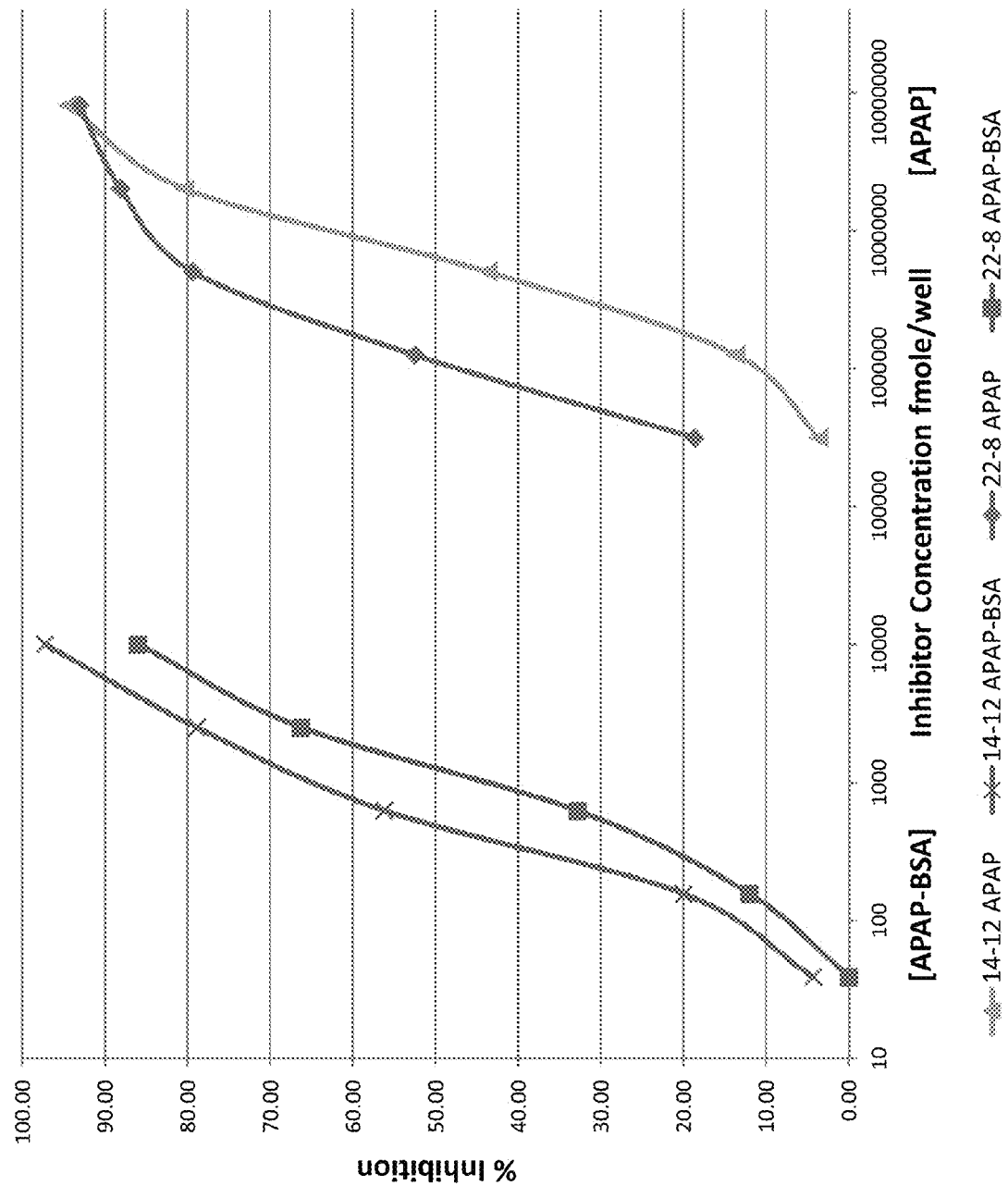
FIG. 3 depicts a competitive ELISA of RMAb clones 14-12 and 22-8. The graph shows the relative potency of parent drug (APAP) versus adduct (APAP-protein) as inhibitor.

As demonstrated above, clone 14-12 antibody has approximately 8000 times more affinity for acetaminophen protein adduct than it does for free APAP as measured in this ELISA context. Additionally, clone 22-8 antibody has approximately 1250 times more affinity for acetaminophen protein adduct than it does for free APAP as measured in this ELISA context (FIG. 3).

Figure 4:
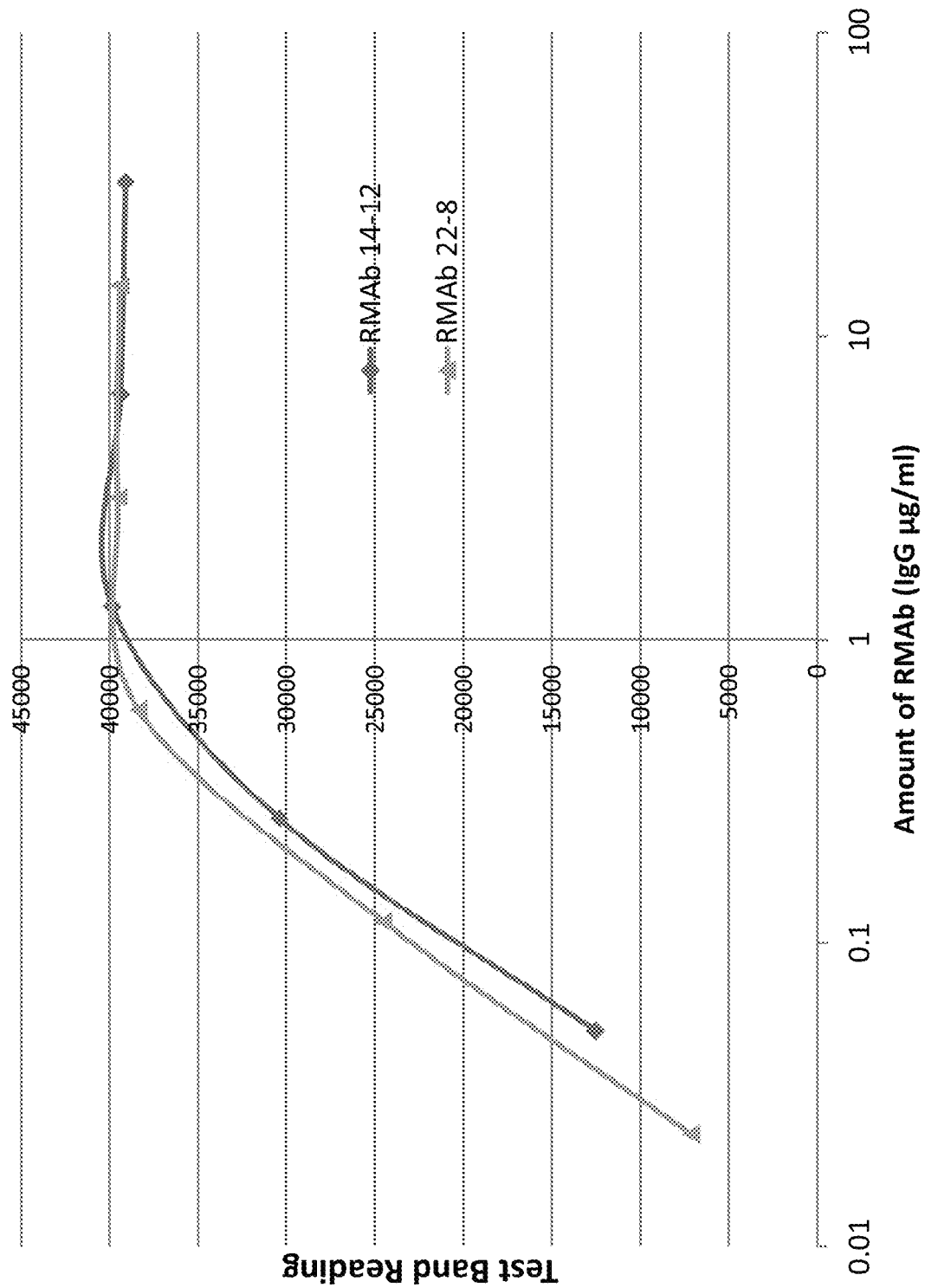
FIG. 4 depicts binding of RMAb 14-12 and 22-8 to acetaminophen protein adduct immobilized at the test band in lateral flow assays.

Example 3. Binding of RMAb to Acetaminophen Protein Adduct Immobilized at Test Band in Lateral Flow Assays Binding of RMAb to acetaminophen protein adduct immobilized at the test band of lateral flow assays was determined by preparing serial dilutions of RMAb in dilution buffer (phosphate buffered saline containing, 0.02% NaN$_3$ and 0.125% (W/V) non-fat dry milk). Bound RMAb was detected using 40 nm nanoparticulate gold adsorbed on Goat anti-Rabbit IgG. The log plot of RMAb (μg/ml IgG) versus Test Band Reading (arbitrary reflectance units) indicates that 0.01 μg RMAb gives a Test Band reflectance of approximately 20,000 (FIG. 4). A value of 0.01 μg was calculated based on that 100 μl of a 0.1 μg/ml solution was used. Subsequent competitive inhibition assays in lateral flow format used this amount of RMAb. Test Band antigen was ovalbumin modified with NAPQI to produce APAP-protein adduct.

Figure 5:
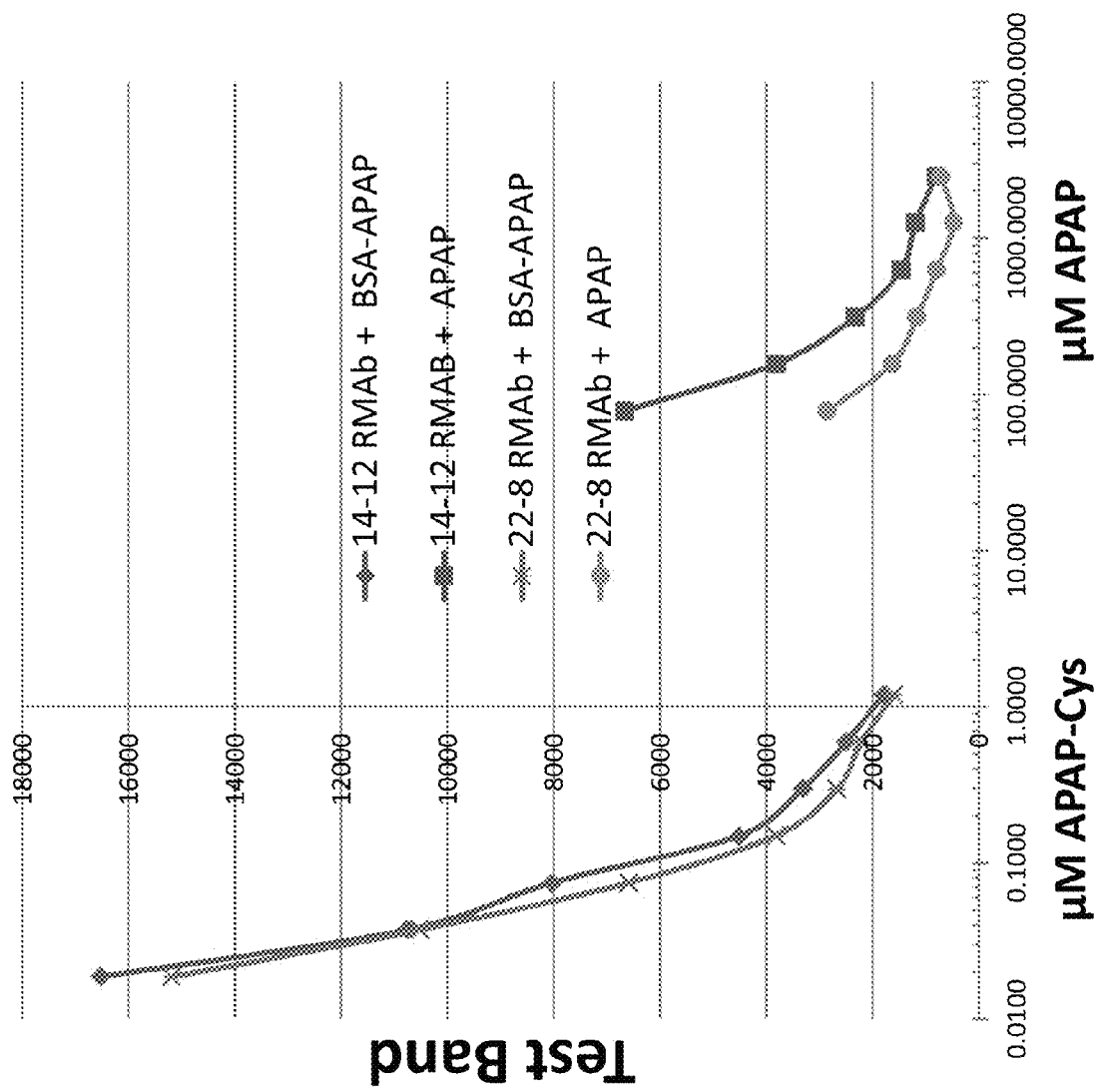
FIG. 5 depicts a competitive lateral flow assay with RMAb 14-12 and 22-8. The graph shows the relative potency of parent drug (APAP) versus adduct (APAP-protein) as inhibitor.

Example 4. Competitive Lateral Flow Immunoassay with RMAb Clones 14-12 and 22-8: Relative Potency of Parent Drug (APAP) Versus Adduct (APAP-Protein) as Inhibitor A competitive inhibition assay using RMAb in lateral flow format was then performed. RMAb was diluted to 0.2 μg/ml and this Ab concentration was combined with an equal volume of inhibitor, either BSA-APAP or APAP, such that the final concentration applied to each 100 μl lateral flow assay was 0.01 μg RMAb and the indicated final concentration of inhibitor. The data indicate that the lateral flow assay using RMAb detected APAP-protein adduct in the range of seven serial 2-fold dilutions from 1.19 to 0.0186 μM and detected APAP in the range six serial 2-fold dilutions of 2500 to 78 μM (final concentrations) (FIG. 5). Collectively the data indicates that the assay is sensitive for the detection of APAP-protein adducts (APAP-Cys) and much less sensitive (>8000-fold) for the detection of APAP. Restated: one mole of APAP-Cys is approximately 8000 times more potent than one mole of APAP for the inhibition of RMAb binding to the APAP-protein adduct immobilized at the test band.

Figure 6:
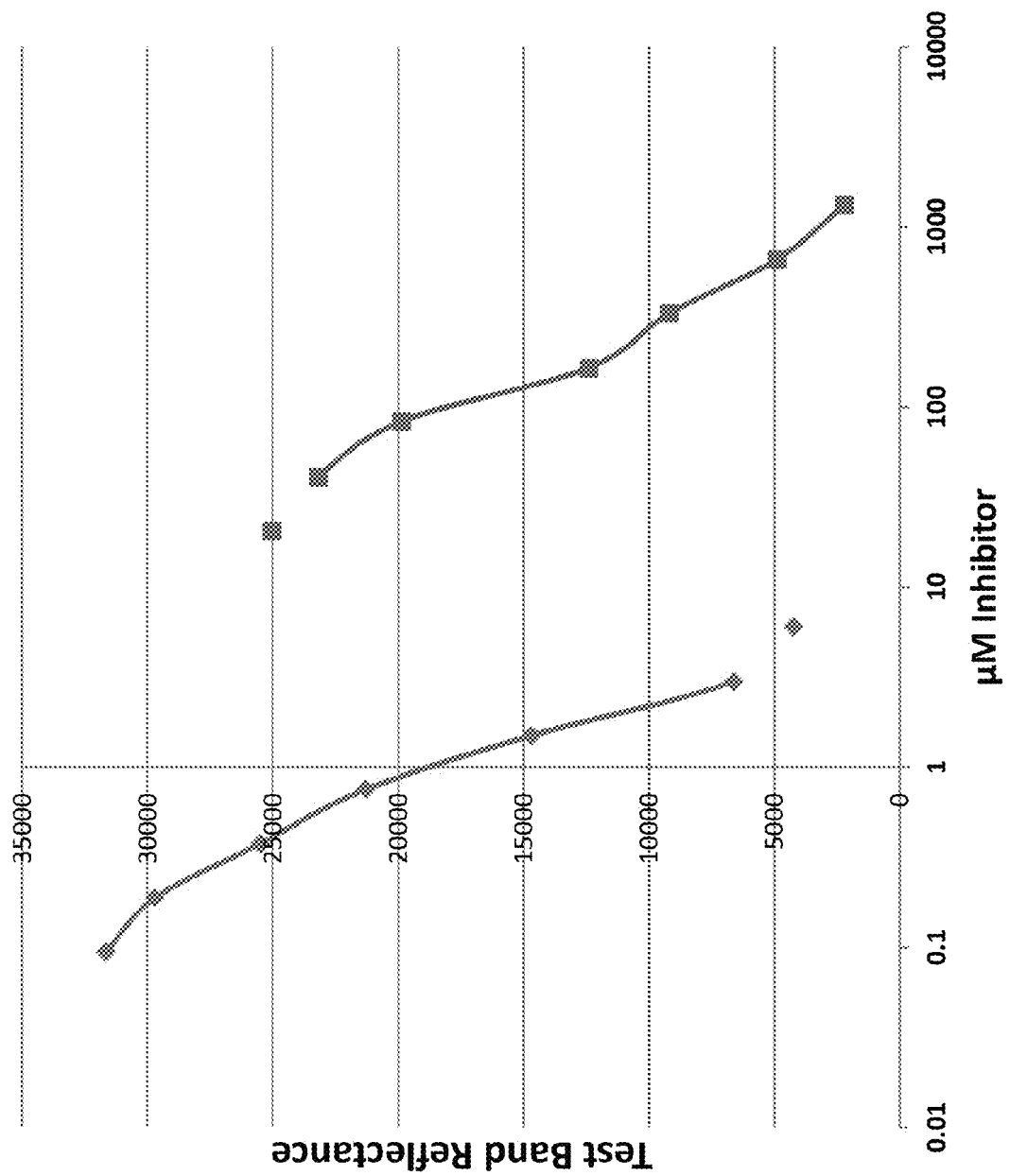
FIG. 6 depicts the inhibition of APAP-protein adducts and APAP in a competitive RMAb-based lateral flow assay. The APAP-protein adduct is physiologically formed APAP protein adduct from the serum of an APAP toxicity patient.

Next, the same competitive assay was performed but instead the APAP-protein adduct was physiologically formed APAP-protein adduct from the serum of an APAP toxicity patient. APAP protein adduct concentration of the inhibitor was determined by HPLC-EC. Human APAP-protein adduct and APAP were diluted in control human serum. The data again demonstrated that the assay is sensitive for the detection of APAP-protein adducts (APAP-Cys) and much less sensitive for the detection of APAP (FIG. 6).

Example 5. Development of Immunoassays for Acetaminophen Toxicity

The identification of NAPQI adducted proteins may allow development of specific immunoassays for acetaminophen toxicity. In one embodiment, protein-specific antibodies may be used in a competitive immunoassay in which a limiting amount of antibody specific for acetaminophen-protein adduct may be mixed with a sample putatively containing acetaminophen-protein adducts and, if present in the sample, the adducts will inhibit the binding of antibody to an immobilized synthetically prepared acetaminophen-protein adduct. This method would measure total adducts (including all acetaminophen-protein adducts regardless of what (cysteine-containing) proteins in the sample were adducted. Typical examples would include the ELISA in FIG. 2 and the Lateral Flow assay in FIG. 5 and FIG. 6.

In another embodiment, protein-specific antibodies may be used to capture and isolate adducted protein(s), and then a second antibody specific for acetaminophen-cysteine adducts (total adducts) may be used to detect the adduction of the protein.

Human acetaminophen overdose and exposure samples may be analyzed to understand the frequency of occurrence of the specific protein adducts among different degrees of severity or circumstances of toxicity. To accomplish this, additional methodology may be developed to antibody/affinity isolate specific proteins that contain cysteine and are thus candidates for adduct formation and thus enrich for the specific adduct proteins from human samples. For example, assays using solid-phase antibodies to a specific protein (on paramagnetic beads or other solid phase matrix) to capture the specific protein may be performed and complimented with detection of adduct proteins using the monoclonal antibodies produced in Example 1 with specificity for APAP bound to protein. Essentially the assay may involve interrogating the adducted protein two times: 1) capture by specific anti-protein antibody, and 2) detection with the antibodies specific for the hapten protein linkage produced in Example 1. Commercially available anti-protein antibodies, or newly-developed antibodies designed specifically for the use described herein, may be used.

Preferably, the assay may involve interrogating the adducted protein by capturing with monoclonal antibodies produced in Example 1 with specificity for the hapten protein linkage, and detecting with antibodies specific for the protein.

What is claimed is:

1. A composition for an immunoassay, the composition comprising at least one isolated antibody which specifically binds an acetaminophen-protein adduct but does not specifically bind free acetaminophen, wherein the antibody comprises: (a) a light chain CDR1 amino acid sequence of SEQ ID NO:21; (b) a light chain CDR2 amino acid sequence of SEQ ID NO:22; (c) a light chain CDR3 amino acid sequence of LGh; wherein h is a hydrophobic amino acid; (d) a heavy chain CDR1 amino acid sequence of YXI, wherein X is any amino acid; (e) a heavy chain CDR2 amino acid sequence of SEQ ID NO:23; and (f) a heavy chain CDR3 amino acid sequence of SEQ ID NO:24.

2. The composition of claim 1, wherein the immunoassay is a competitive or a non-competitive immune assay.

3. The composition of claim 1, wherein the immunoassay is selected from the group consisting of an enzyme linked immunosorbent assay (ELISA), a lateral flow assay, a sandwich immunoassay, a radioimmunoassay, an immunoblot or Western blot, flow cytometry, immunohistochemistry, and an antibody array.

4. A composition for an immunoassay, the composition comprising at least one isolated antibody which specifically binds an acetaminophen-protein adduct but does not specifically bind free acetaminophen, wherein the antibody comprises: (a) a light chain CDR1 amino acid sequence of SEQ ID NO:21; (b) a light chain CDR2 amino acid sequence of SEQ ID NO:22; (c) a light chain CDR3 amino acid sequence of LGh; wherein h is a hydrophobic amino acid; (d) a heavy chain CDR1 amino acid sequence of YXI, wherein X is any amino acid; (e) a heavy chain CDR2 amino acid sequence of SEQ ID NO:23; and (f) a heavy chain CDR3 comprising the amino acid sequence of SEQ ID NO:6 with zero to two amino acid substitutions or SEQ ID NO:12 with zero to two amino acid substitutions.

5. The composition of claim 4, wherein the immunoassay is a competitive or a non-competitive immune assay.

6. The composition of claim 4, wherein the immunoassay is selected from the group consisting of an enzyme linked immunosorbent assay (ELISA), a lateral flow assay, a sandwich immunoassay, a radioimmunoassay, an immunoblot or Western blot, flow cytometry, immunohistochemistry, and an antibody array.

7. A composition for an immunoassay, the composition comprising at least one isolated antibody which specifically binds an acetaminophen-protein adduct but does not specifically bind free acetaminophen, wherein the antibody comprises: (a) a light chain CDR1 amino acid sequence of SEQ ID NO:21; (b) a light chain CDR2 amino acid sequence of SEQ ID NO:22; (c) a light chain CDR3 comprising the amino acid sequence of SEQ ID NO:3 with zero to two amino acid substitutions or SEQ ID NO:9 with zero to two amino acid substitutions; (d) a heavy chain CDR1 amino acid sequence of YXI, wherein X is any amino acid; (e) a heavy chain CDR2 amino acid sequence of SEQ ID NO:23; and (f) a heavy chain CDR3 amino acid sequence of SEQ ID NO:24.

8. The composition of claim 7, wherein the immunoassay is a competitive or a non-competitive immune assay.

9. The composition of claim 7, wherein the immunoassay is selected from the group consisting of an enzyme linked immunosorbent assay (ELISA), a lateral flow assay, a sandwich immunoassay, a radioimmunoassay, an immunoblot or Western blot, flow cytometry, immunohistochemistry, and an antibody array.

\* \* \* \* \*